US012390342B2

(12) United States Patent
Joly et al.

(10) Patent No.: US 12,390,342 B2
(45) Date of Patent: Aug. 19, 2025

(54) VERTEBRAL SYSTEM, IMPLANT AND INSERTS FOR VERTEBRAL SYSTEM

(71) Applicant: LDR Medical, S.A.S., Sainte-Savine (FR)

(72) Inventors: Florian Joly, La Riviere de Corps (FR); Edouard Jouan, Lavau (FR); Alexis Mercier, Verrieres (FR); Thierry Millard, Cestas (FR)

(73) Assignee: LDR Medical, S.A.S. (FR)

( * ) Notice: Subject to any disclaimer, the term of this patent is extended or adjusted under 35 U.S.C. 154(b) by 343 days.

(21) Appl. No.: 17/488,973

(22) Filed: Sep. 29, 2021

(65) Prior Publication Data
US 2022/0015925 A1 Jan. 20, 2022

Related U.S. Application Data

(63) Continuation of application No. 16/453,592, filed on Jun. 26, 2019, now Pat. No. 11,154,406, which is a
(Continued)

(30) Foreign Application Priority Data

May 3, 2016 (FR) ..................................... 1653981

(51) Int. Cl.
*A61F 2/44* (2006.01)
*A61F 2/28* (2006.01)
*A61F 2/30* (2006.01)

(52) U.S. Cl.
CPC ........ *A61F 2/4465* (2013.01); *A61F 2/30734* (2013.01); *A61F 2/30771* (2013.01);
(Continued)

(58) Field of Classification Search
CPC .................. A61F 2/4465; A61F 2/4455; A61F 2002/4495; A61F 2/3074; A61F 2/30771; A61F 2002/30772
See application file for complete search history.

(56) References Cited

U.S. PATENT DOCUMENTS

| 5,888,223 A | 3/1999 | Bray, Jr. |
| 8,900,311 B2 * | 12/2014 | Ciupik .................. A61F 2/4465 623/17.16 |

(Continued)

FOREIGN PATENT DOCUMENTS

| DE | 202013006283 U1 | 4/2014 |
| EP | 0770367 A1 | 5/1997 |

(Continued)

OTHER PUBLICATIONS

"U.S. Appl. No. 15/586,003, Non Final Office Action mailed Oct. 12, 2018", 8 pgs.
(Continued)

*Primary Examiner* — Matthew J Lawson
(74) *Attorney, Agent, or Firm* — Sheridan Ross P.C.

(57) ABSTRACT

The present invention relates to a vertebral system comprising a vertebral implant (2) and a plurality of inserts, said implant being designed to be implanted in a vertebral segment composed of at least two vertebrae and including a body (20) the walls whereof delimit a cavity (23) leading to the outside of the body (20) through at least one opening in at least one of said walls, at least one passage (21) passing through the implant (2) from the periphery to an upper or lower surface to receive a bone-anchoring device (1) capable of anchoring the implant (2) in at least one of said vertebrae, the system being characterized in that it includes at least two inserts selected from among the following inserts:
at least one graft insert (3, 3A, 3B, 4, 5A, 5B, 6A, 6B, 6C, 6D, 202, 250) capable of being colonized by bone
(Continued)

tissue and/or receiving at least one bone tissue graft and/or at least one substitute;
and/or
at least one bone-anchoring insert (210) comprising said passage (21) capable of receiving said bone-anchoring device (1).

20 Claims, 22 Drawing Sheets

Related U.S. Application Data continuation of application No. 15/586,003, filed on May 3, 2017, now Pat. No. 10,369,009, which is a continuation of application No. PCT/EP2017/060587, filed on May 3, 2017.

(52) U.S. Cl.
CPC .............. *A61F 2/44* (2013.01); *A61F 2/4455* (2013.01); *A61F 2/28* (2013.01); *A61F 2002/2835* (2013.01); *A61F 2002/30011* (2013.01); *A61F 2002/30148* (2013.01); *A61F 2002/30331* (2013.01); *A61F 2002/30383* (2013.01); *A61F 2002/30481* (2013.01); *A61F 2002/30579* (2013.01); *A61F 2002/30593* (2013.01); *A61F 2002/30604* (2013.01); *A61F 2002/30733* (2013.01); *A61F 2002/30774* (2013.01); *A61F 2002/30785* (2013.01); *A61F 2002/30787* (2013.01); *A61F 2002/30828* (2013.01); *A61F 2002/30841* (2013.01); *A61F 2002/30879* (2013.01); *A61F 2002/30904* (2013.01); *A61F 2002/30909* (2013.01); *A61F 2002/30911* (2013.01); *A61F 2002/3092* (2013.01); *A61F 2002/3093* (2013.01); *A61F 2002/30985* (2013.01); *A61F 2002/4495* (2013.01)

(56) References Cited

U.S. PATENT DOCUMENTS

| | | | |
|---|---|---|---|
| 9,486,327 B2 | 11/2016 | Martynova et al. | |
| 10,226,357 B2 | 3/2019 | Ries | |
| 10,271,958 B2 | 4/2019 | Schaufler et al. | |
| 10,369,009 B2 | 8/2019 | Joly et al. | |
| 10,420,597 B2* | 9/2019 | Papangelou | A61B 17/0401 |
| 11,969,356 B2* | 4/2024 | Laurence | A61F 2/442 |
| 12,127,953 B2* | 10/2024 | Niemiec | A61F 2/447 |
| 2005/0027364 A1* | 2/2005 | Kim | A61F 2/4425 |
| | | | 623/17.13 |
| 2006/0293748 A1* | 12/2006 | Alexander | A61F 2/4611 |
| | | | 623/908 |
| 2007/0260324 A1 | 11/2007 | Joshi | |
| 2009/0105824 A1 | 4/2009 | Jones et al. | |
| 2010/0286783 A1* | 11/2010 | Lechmann | B33Y 80/00 |
| | | | 623/17.11 |
| 2011/0172775 A1* | 7/2011 | Flickinger | A61F 2/4465 |
| | | | 623/17.16 |
| 2011/0190888 A1* | 8/2011 | Bertele | A61F 2/447 |
| | | | 623/17.11 |
| 2011/0224796 A1 | 9/2011 | Weiland et al. | |
| 2011/0313532 A1 | 12/2011 | Hunt | |
| 2013/0096685 A1 | 4/2013 | Ciupik et al. | |
| 2013/0116793 A1 | 5/2013 | Kloss | |
| 2013/0226300 A1 | 8/2013 | Chataigner et al. | |
| 2013/0325129 A1* | 12/2013 | Huang | A61F 2/44 |
| | | | 623/17.16 |
| 2014/0088711 A1* | 3/2014 | Chin | A61F 2/30749 |
| | | | 623/17.16 |
| 2015/0238324 A1 | 8/2015 | Nebosky et al. | |
| 2015/0250607 A1* | 9/2015 | Drochner | A61F 2/447 |
| | | | 623/17.11 |
| 2015/0328010 A1 | 11/2015 | Martynova et al. | |
| 2016/0193055 A1* | 7/2016 | Ries | A61F 2/4455 |
| | | | 623/17.16 |
| 2017/0020685 A1 | 1/2017 | Geisler et al. | |
| 2017/0333205 A1 | 11/2017 | Joly et al. | |
| 2019/0336305 A1 | 11/2019 | Joly et al. | |

FOREIGN PATENT DOCUMENTS

| | | |
|---|---|---|
| WO | WO-2013019543 A2 | 2/2013 |
| WO | WO-2017191223 A1 | 11/2017 |

OTHER PUBLICATIONS

"U.S. Appl. No. 15/586,003, Notice of Allowance mailed Mar. 27, 2019", 5 pgs.
"U.S. Appl. No. 15/586,003, Preliminary Amendment filed May 3, 2017", 5 pgs.
"U.S. Appl. No. 15/586,003, Response filed Jan. 11, 2019 to Non Final Office Action mailed Oct. 12, 2018", 11 pgs.
"U.S. Appl. No. 15/586,003, Response filed Aug. 22, 2018 to Restriction Requirement mailed Jun. 22, 2018", 7 pgs.
"U.S. Appl. No. 15/586,003, Restriction Requirement mailed Jun. 22, 2018", 6 pgs.
"U.S. Appl. No. 16/453,592, Examiner Interview Summary mailed Jun. 18, 2021", 2 pgs.
"U.S. Appl. No. 16/453,592, Final Office Action mailed Apr. 19, 2021", 8 pgs.
"U.S. Appl. No. 16/453,592, Non Final Office Action mailed Jan. 15, 2021", 7 pgs.
"U.S. Appl. No. 16/453,592, Notice of Allowance mailed Jun. 29, 2021", 5 pgs.
"U.S. Appl. No. 16/453,592, Preliminary Amendment filed Jul. 30, 2019", 6 pgs.
"U.S. Appl. No. 16/453,592, Response filed Apr. 6, 2021 to Non Final Office Action mailed Jan. 15, 2021", 7 pgs.
"U.S. Appl. No. 16/453,592, Response filed Jun. 18, 2021 to Final Office Action mailed Apr. 19, 2021", 8 pgs.
International Search Report and Written Opinion for International (PCT) Patent Application No. PCT/EP2017060587, dated Aug. 2, 2017 17 pages.
Preliminary Report on Patentability (with English translation) for International (PCT) Patent Application No. PCT/EP2017060587, dated Nov. 15, 2018 12 pages.
Official Action for European Patent Application No. 17725522.1, dated Oct. 18, 2023 5 pages.

* cited by examiner

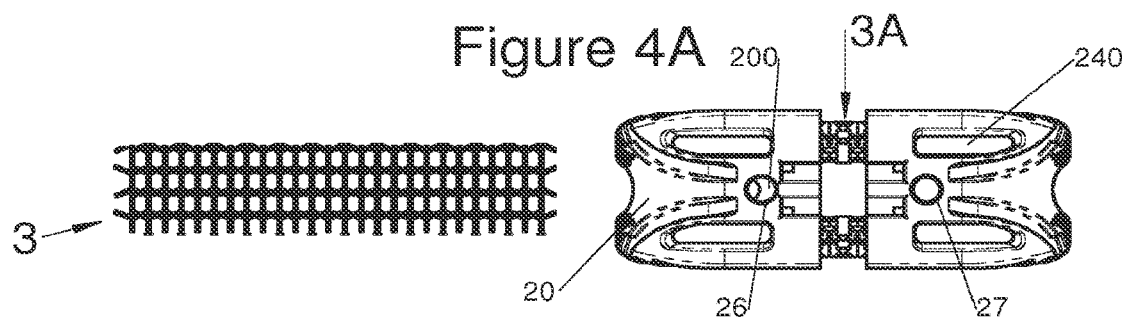
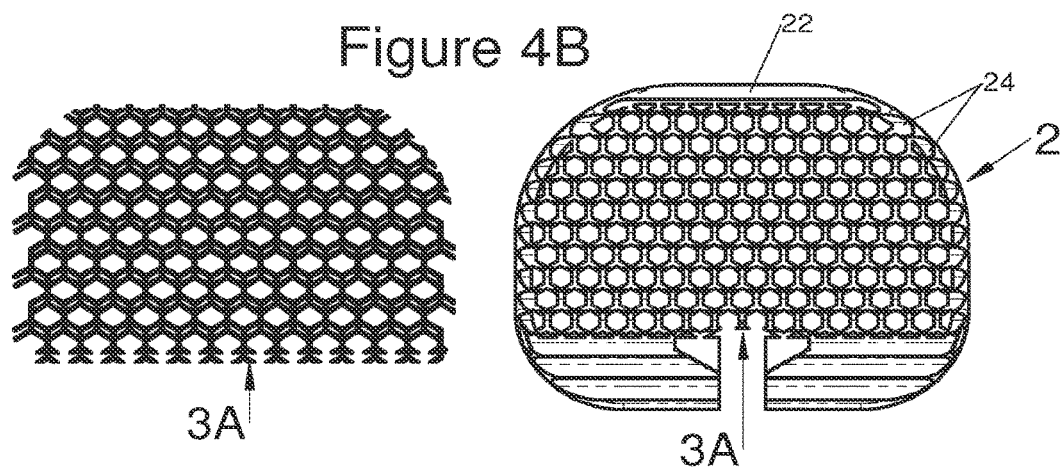
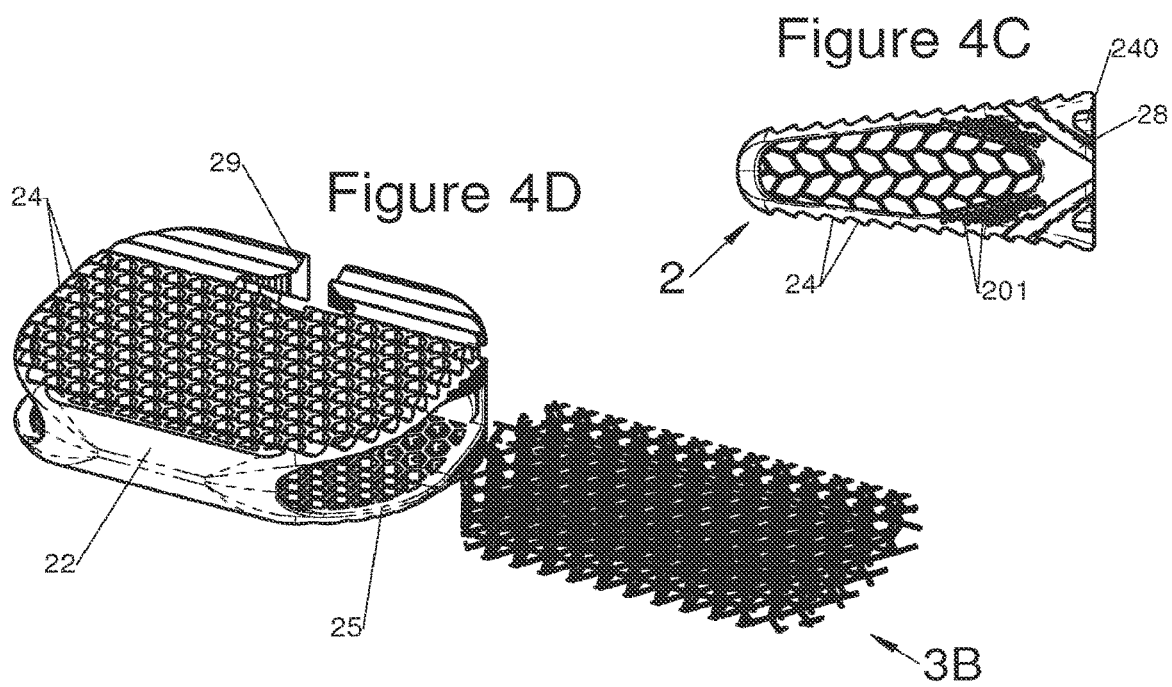

Figure 5A
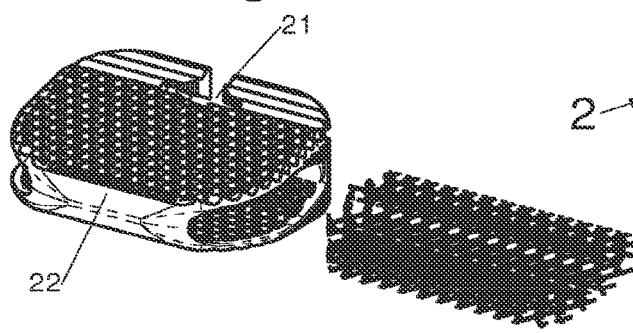
Figure 5B
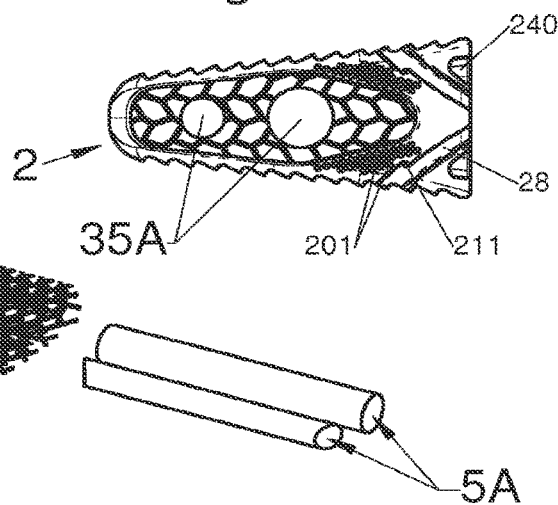
Figure 5C
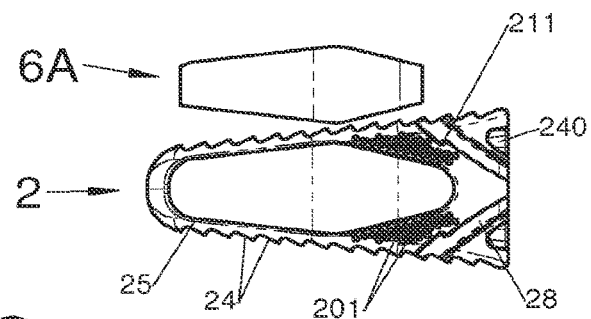
Figure 5D
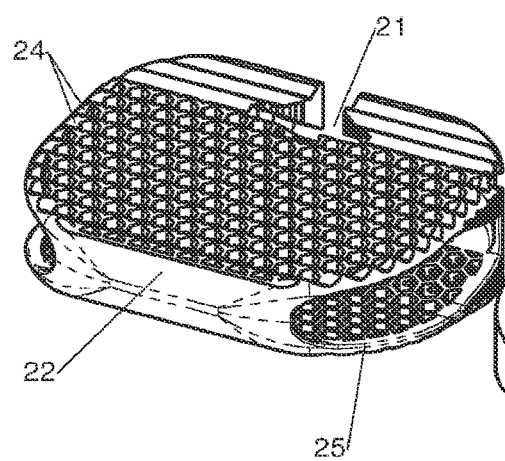
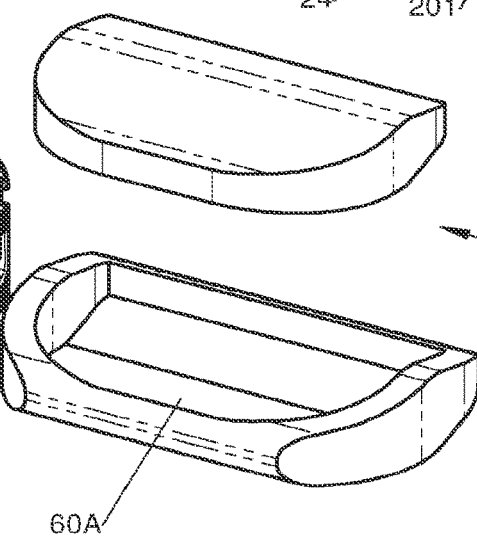

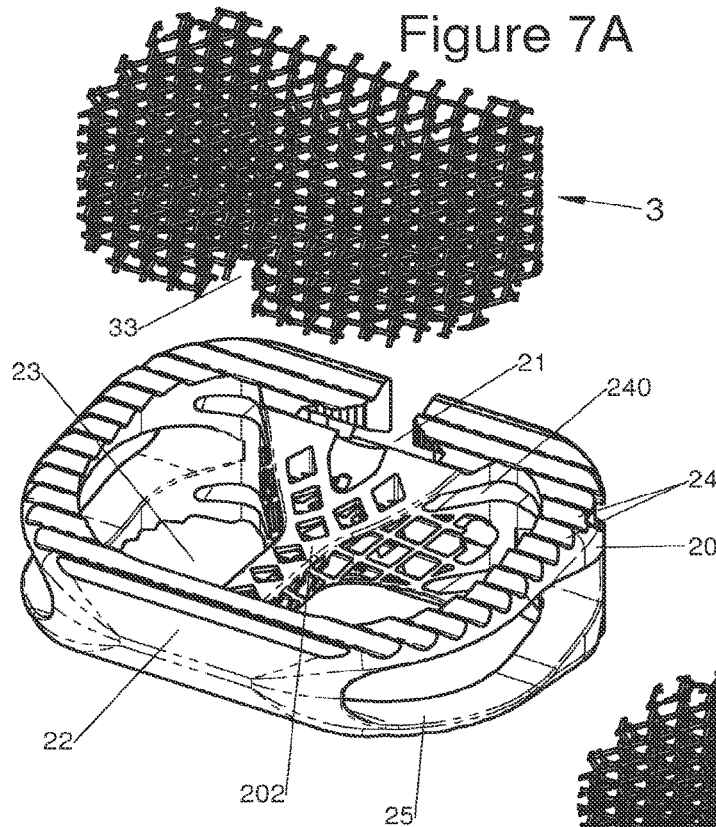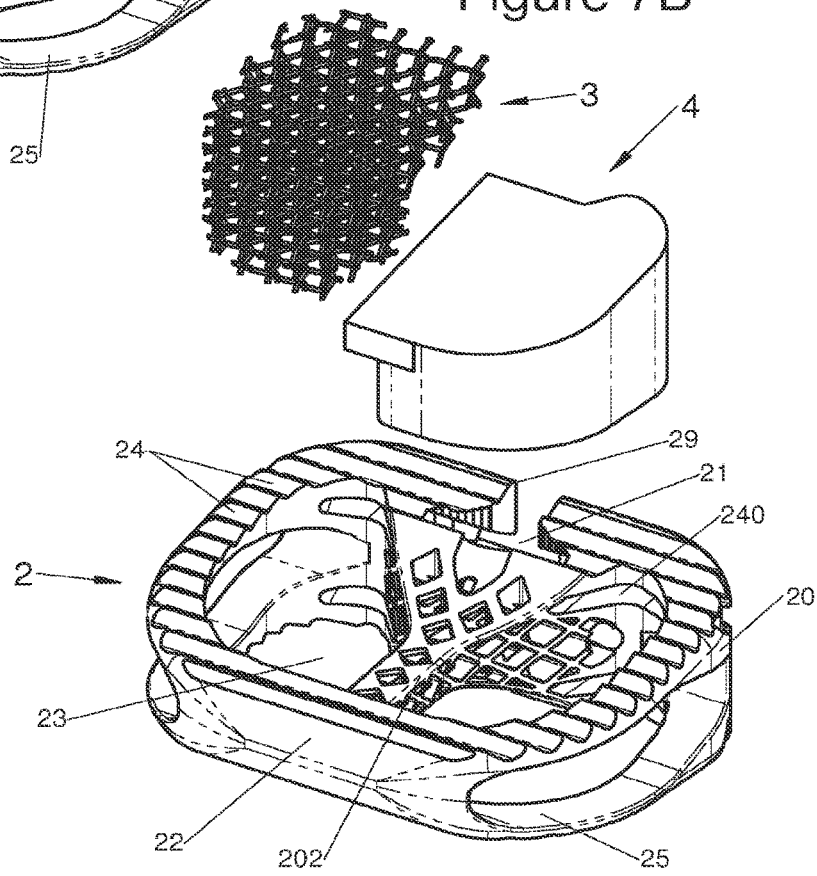

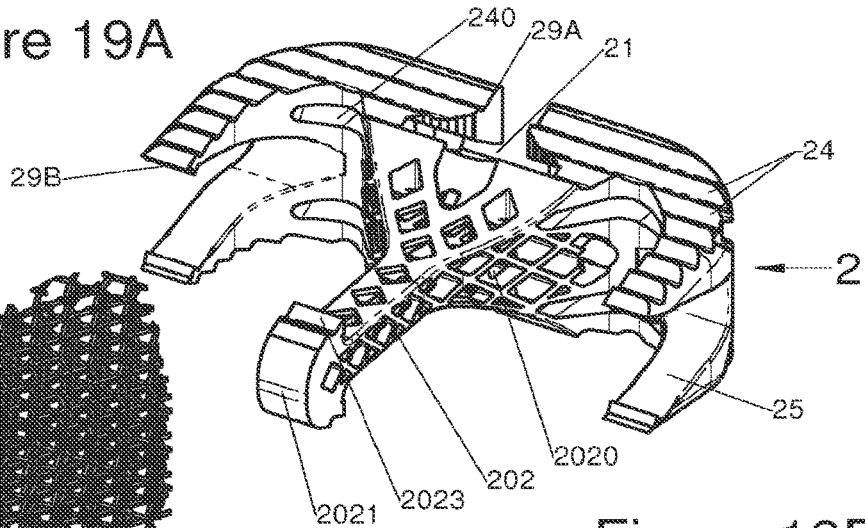
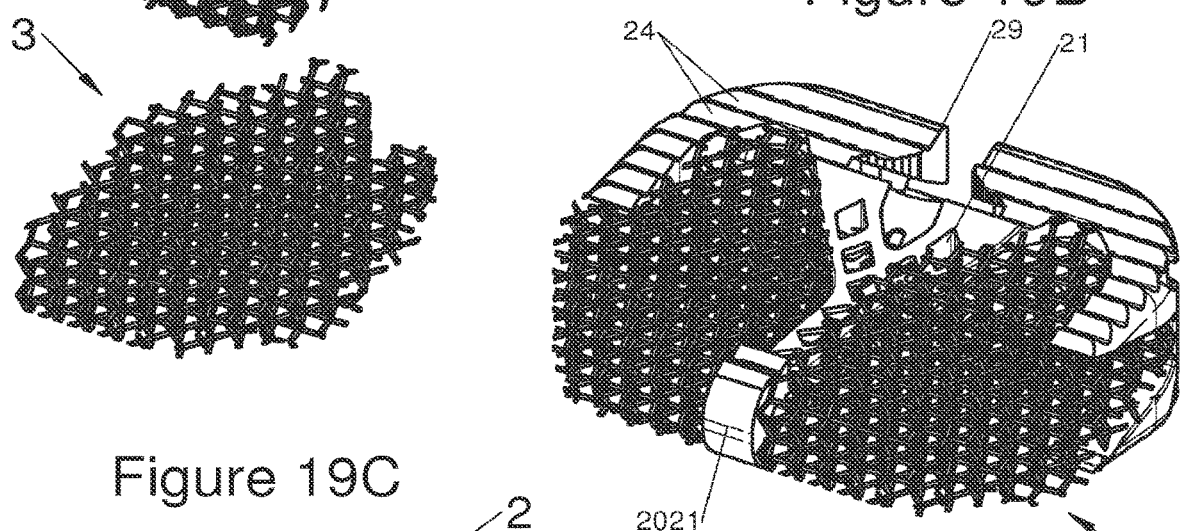
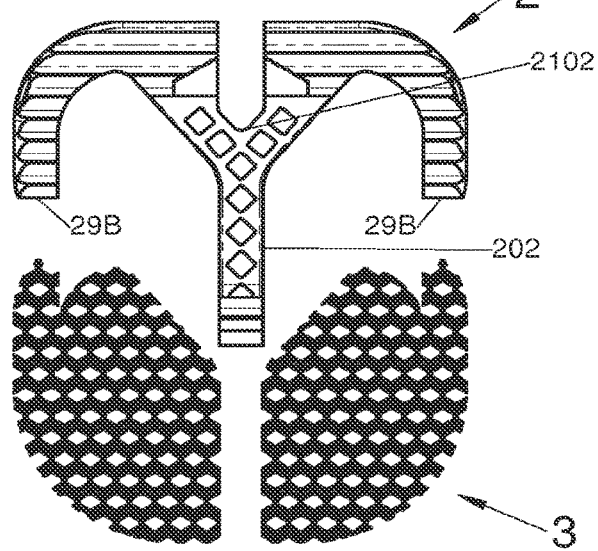
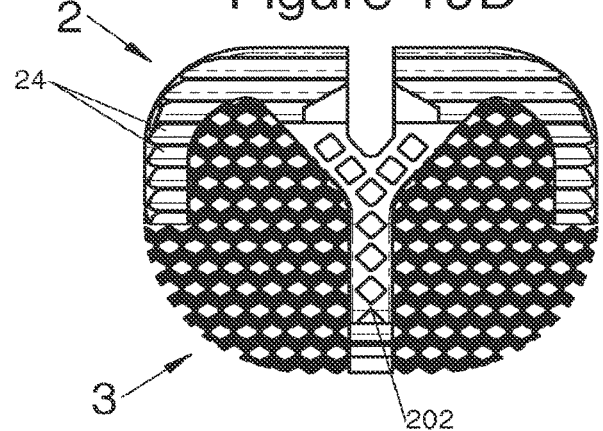

VERTEBRAL SYSTEM, IMPLANT AND INSERTS FOR VERTEBRAL SYSTEM

CROSS REFERENCE TO RELATED APPLICATIONS

The present application is a continuation of U.S. patent application Ser. No. 16/453,592, filed Jun. 26, 2019, now U.S. Pat. No. 11,154,406, which is a continuation of U.S. patent application Ser. No. 15/586,003, filed May 3, 2017, now U.S. Pat. No. 10,369,009, which is a continuation of PCT/EP2017/060587, filed May 3, 2017 and claims priority to France 1653981, filed May 3, 2016, all of which are incorporated herein by this reference in its entirety.

TECHNICAL FIELD OF THE INVENTION

The present invention relates to the field of orthopedic surgery, and in particular to spinal surgery. The present invention relates more particularly to a modular vertebral implant, particularly through the use of various graft inserts and/or attachment inserts, but it also relates to at least one (modular) insert for such a modular implant and a modular (adjustable) implant system with modular inserts.

BACKGROUND OF THE INVENTION

One problem in the field of orthopedic implants and in particular of spinal implants relates to arthrodesis, i.e. the fusion of two bone structures, which is often desirable or necessary to accomplish to treat a patient. The success of this type of treatment depends in general on the speed and/or the reliability of the bone fusion obtained. This speed and this reliability are often linked, and are often based on the quality of the immobilization of the two bone structures that it is desired to fuse. Thus, a second problem in the field relates to the attachment of bone implants and in particular the reliability of that attachment. Moreover, in the particular case of the spine, these problems are accompanied by various problems and constraints connected with crowding around the sites to be treated. In fact, obtaining fusion of at least two vertebrae is sometimes attempted, for example when at least one of their adjacent inter-vertebral disks is damaged. Known from the prior art are various arthrodesis techniques, based on various types of implants, such as intersomatic (or arthrodesis) cages for example, inserted in place of a disk to promote bone growth, or the corpectomy cages which replace a vertebral segment sometimes containing at least a portion of at least one vertebral body, generally in addition to at least one intervertebral disk. Also known, particularly at the lumbar or sacral level, are solutions using facet implants (inter-facet or trans-facet) allowing attachment of the articular facets of two vertebrae for the purpose of obtaining fusion between them. Generally, these various solutions aim to resolve, in addition, the problem of the stability of the implant and of the vertebral structures treated. It is necessary that an implant be stable in its implantation site, in particular when an arthrodesis is desired because the latter must take place in a relative position of the elements of the spine which is optimal (as desired by the surgeon). Stabilization and/or locking of the implant is (are) therefore preferable.

These solutions have the disadvantages of not always responding correctly to the general problems of facility and/or speed of implantation and of the invasiveness of the implants and of the surgical techniques which depend on them. In fact, it is generally desired that the implants be able to be is implanted quickly and/or easily, with minimal invasiveness, i.e. it is desired to limit the size of the incisions and of the damage to the surrounding tissue. This problem of invasiveness relates in particular to the introduction of implants into the spine and particularly to access to the intervertebral spaces (disc spaces) which is often particularly delicate due to crowding, due for example to the presence of blood vessels and of nerves around the intervertebral space, as well as the proximity of the spinal cord.

Finally, another problem in the field of implants relates to the variability of individuals and pathologies. For example, the size of vertebrae is highly variable depending on the individuals and depending on the position in the spinal column, but the great variability of disorders and pathologies of the patients makes the design of implants even more complex. To have available usable implants to respond to the needs of a greater number of patients, it is necessary to provide a large number of implants which differ in size and/or in the inclination of their bone contact surfaces and/or in their bone anchoring, etc. This multiplicity of necessary implants presents a major disadvantage in cost of production and in stock management. Moreover, a problem which is derived implicitly from those mentioned above relates to the fact that it is sometimes useful to supply a system of implants (particularly for arthrodesis) the bone anchoring whereof can vary depending on needs, or even be decided at the last moment, i.e. just before the implantation of the system into the patient, or even actually during the implantation. In fact, the surgeon can sometimes desire to change the type of bone anchoring by providing bone anchoring means which exert a compression on the vertebrae around the implant system (i.e. which tend to bring the two adjacent vertebra closer to one another), as for example by bone anchoring means such as screws or anchors the curvature whereof is suited to such an effect (as described in certain documents of the prior art). Moreover, the surgeon may desire (on the same vertebral level of the same patient or on another vertebral level of any patient) that the anchorage not constrain the vertebra in certain directions, or in any direction (including the compression direction). The surgeon is often confronted with problems connected with the selection of the type of is attachment, sometimes up to the moment where he proceeds with the surgery, while the prosthesis supplier is confronted with problems connected to cost and stock management while facilitating the surgery for the surgeon.

In this context, it is attractive to propose a solution which can respond to at least a portion of these problems.

GENERAL DESCRIPTION OF THE INVENTION

The present invention has as its aim to obviate certain drawbacks of the prior art by proposing a vertebral implant, intervertebral in particular, and inserts for this implant, but preferably rather a system (e.g. a kit or an assembly) comprising at least one vertebral implant and a plurality of inserts associated (or associable/assemblable) with this type of implant, so as to form a system which is reliable, fast and usable in a great number of cases, while preferably limiting the costs and the stocks (particularly for suppliers of such systems).

This aim is attained by a modular vertebral arthrodesis system, comprising at least one vertebral implant (2) and a plurality of inserts which can be integrated into said implant, said vertebral implant (2) being designed to be implanted in a vertebral segment composed of at least two vertebrae and including, on the one hand, at least one body (20) the walls whereof delimit a cavity (23) leading to the outside of the body (20) through at least one opening in at least one of said walls and, on the other hand, at least one passage (21) passing through the implant (2) from the periphery toward an upper or lower surface to receive a bone-anchoring device (1) capable of anchoring said implant (2) in at least one of said vertebrae, said system being characterized in that said plurality of inserts includes at least two inserts selected from among the following inserts:

at least one graft insert (3, 3A, 3B, 4, 5A, 5B, 6A, 6B, 6C, 6D, 202, 250) capable of being colonized by bone tissue and/or receiving at least one bone tissue graft and/or at least one substitute;

and/or at least one bone-anchoring insert (210) comprising said passage (21) capable of receiving said bone-anchoring device (1).

According to another special feature, the shapes and dimensions of said opening in at least one of said walls of the implant are complementary, at least in one plane, to the shapes and dimensions of the graft insert and/or the bone-anchoring insert, so that the insertion of the latter item (or the latter items) inside the body of the implant is accomplished through said opening.

According to another special feature, the shapes and dimensions of said opening in one or more of said walls of the implant are complementary to the shapes and dimensions of the graft insert and/or the bone-anchoring insert, which for their part are complementary to one another.

According to another special feature, the implant includes at least one graft insert, but said passage is provided directly in at least one of said walls of the body without requiring a bone-anchoring insert.

According to another special feature, the implant includes at least one bone-anchoring insert, but said cavity is configured to receive directly a bone tissue graft or a substitute, without a graft insert.

According to another special feature, the graft insert comprises at least the following elements:

a meshed modular element;

a solid modular element;

a loading element, called a cassette, capable of receiving at least one such meshed or solid modular element or a graft or a substitute directly.

According to another special feature, the graft insert includes at least one solid or meshed reinforcement.

According to another special feature, said bone-anchoring insert and said body of the implant include reciprocal means for locking said bone-anchoring insert in the implant.

According to another special feature, the posterior portion of the body of the implant comprises an opening capable of receiving said bone-anchoring insert.

According to another special feature, said opening extends from the upper surface to the lower surface of the body and provides a space between two opposite surfaces in the walls of the posterior portion of the body.

According to another special feature, the reciprocal means for locking said bone-anchoring insert into the implant are arranged inside said opening and on the edges of said bone-anchoring insert.

According to another special feature, the posterior portion of the body comprises at least one fastening means designed to cooperate with a gripping end of an instrument for implantation of the implant.

According to another special feature, the meshed modular element comprises at least one recess configured to receive at least one bone graft or substitute and/or at least one solid modular element inside the cavity.

According to another special feature, the meshed modular element includes a three-dimensional network comprising interconnected adjacent planes, each plane being formed of meshes.

According to another special feature, the three-dimensional network of the meshed modular element is obtained by a three-dimensional printing technique or additive manufacturing.

According to another special feature, the attachment insert comprises at least one abutment surface separating two passages and on which bears the posterior portion of the anchoring device, said abutment allowing the device implanted in the vertebra through the passage to be kept stable.

According to another special feature, the implant comprises at least one hollow separating two abutment surfaces.

According to another special feature, the upper and lower surface of the reinforcement are located, respectively, lower and higher than the respectively upper and lower surfaces of the implant, thus allowing the implant to assume possible irregularities of shape of the vertebral end-plates.

According to another special feature, the meshed modular element comprises at least one recess capable of receiving and/or assuming the shape of at least one reinforcement.

According to another special feature, said graft insert forms a cover which does not fill said cavity of the implant, thus leaving free a portion of said cavity, for receiving bone graft or substitute for example.

The present invention also has the aim of mitigating certain disadvantages of the prior art by proposing in particular:

at least one implant capable of receiving at least one insert such as those of the system according to different embodiments of the invention and/or at least one insert for such a vertebral implant so as to form a system which is reliable and quick to implant and makes it possible to use the implant in a large number of cases, while preferably limiting costs and stocks.

This aim is attained by an implant and/or at least one graft insert and/or at least one anchoring insert, preferably at least one implant associated with a plurality of inserts, said inserts each including shapes and dimensions complementary to a body or skeleton of an implant in which said inserts are designed to be inserted for forming said system or implant.

DESCRIPTION OF THE ILLUSTRATIVE FIGURES

Other features and advantages of the present invention will appear more clearly upon reading the description hereafter, made with reference to the appended drawings, wherein.

Figure 3A:
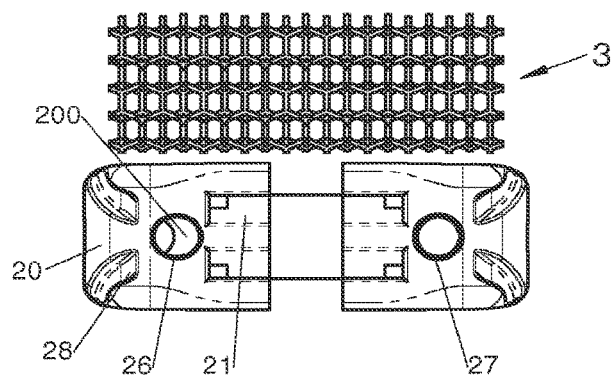
Figure 3B:
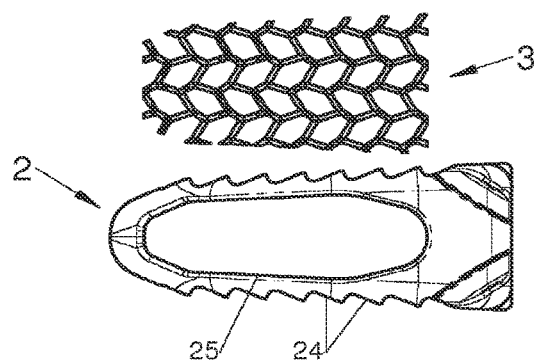
Figure 3C:
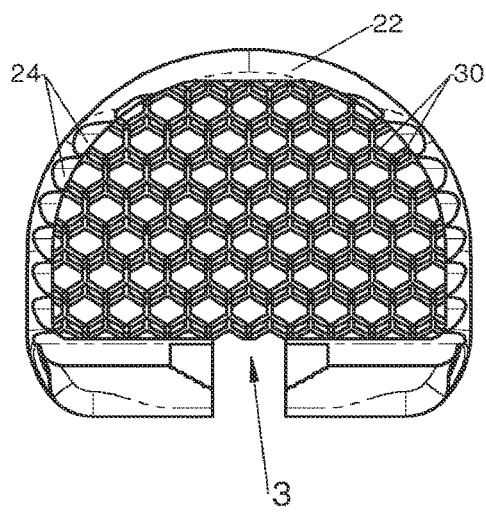
Figure 3D:
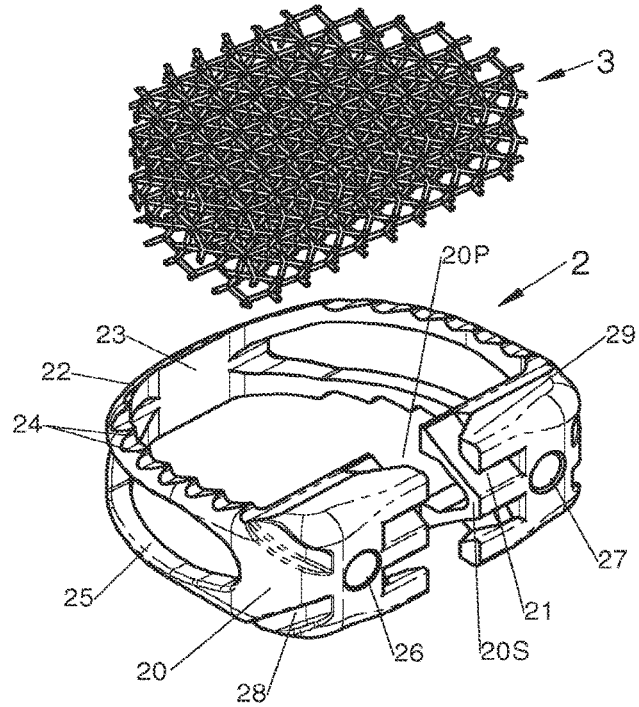

FIGS. 3A, 3B, and 3D show respectively a rear face view, a profile view and a perspective view of an embodiment of an intervertebral implant capable of receiving a graft insert and of a graft insert before assembly, FIG. 3C shows a bottom view of this implant and of this insert after assembly;

FIGS. 4A, 4B and 4D show respectively a rear face view, a top view and a perspective view of an embodiment of an intervertebral implant capable of receiving a graft insert and of a graft insert before assembly, FIG. 4C shows a profile view of this implant and of this insert after assembly.

Figure 6:
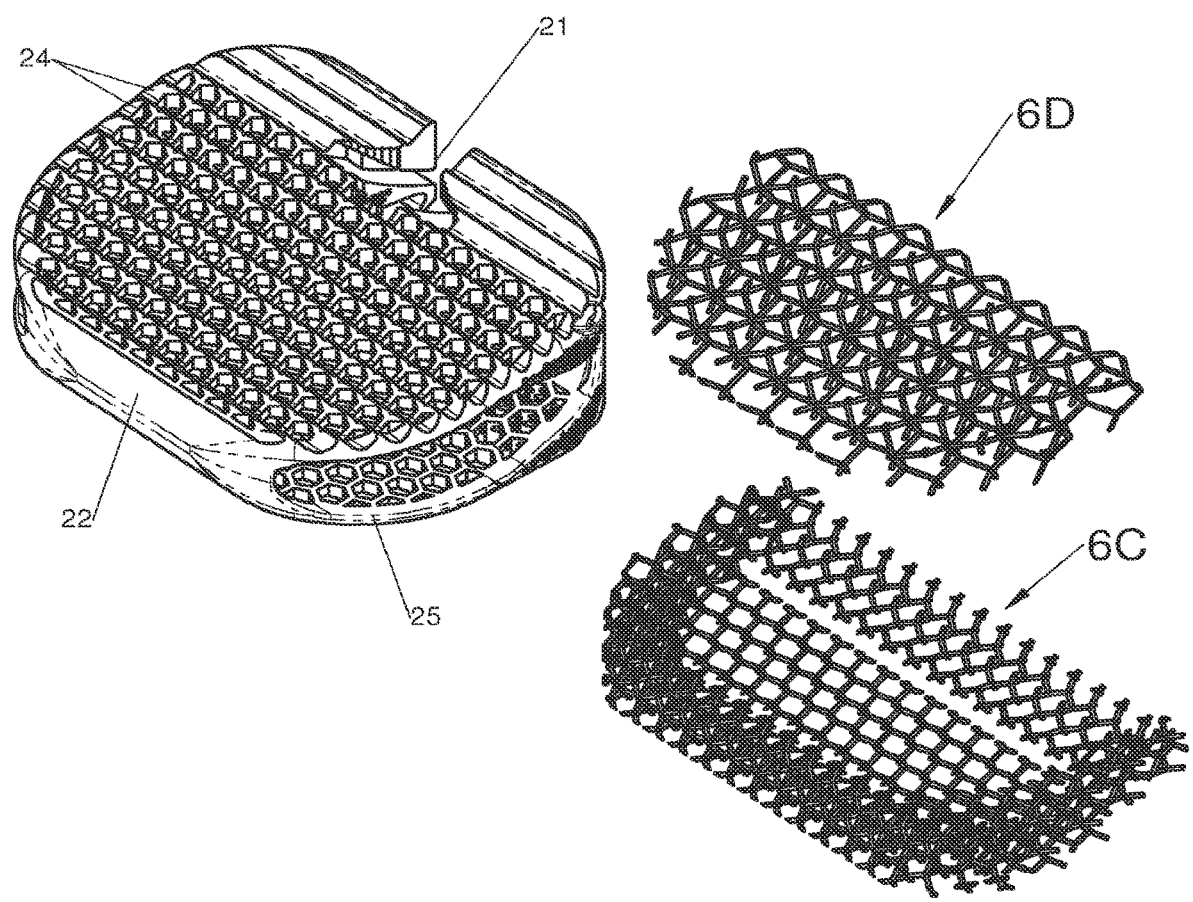
Figure 8A:
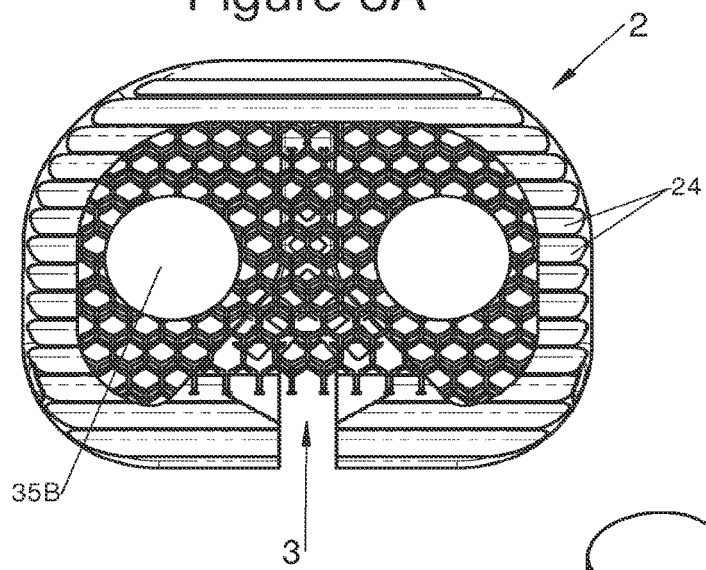
Figure 8B:
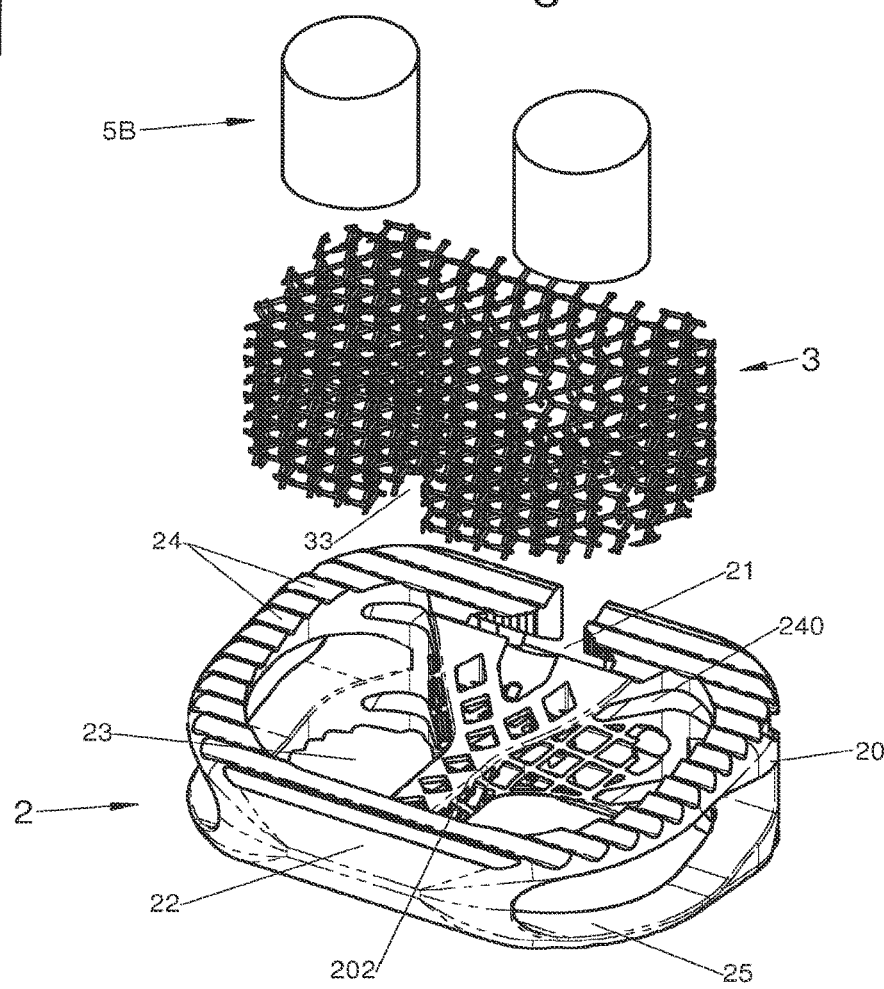
Figure 9A:
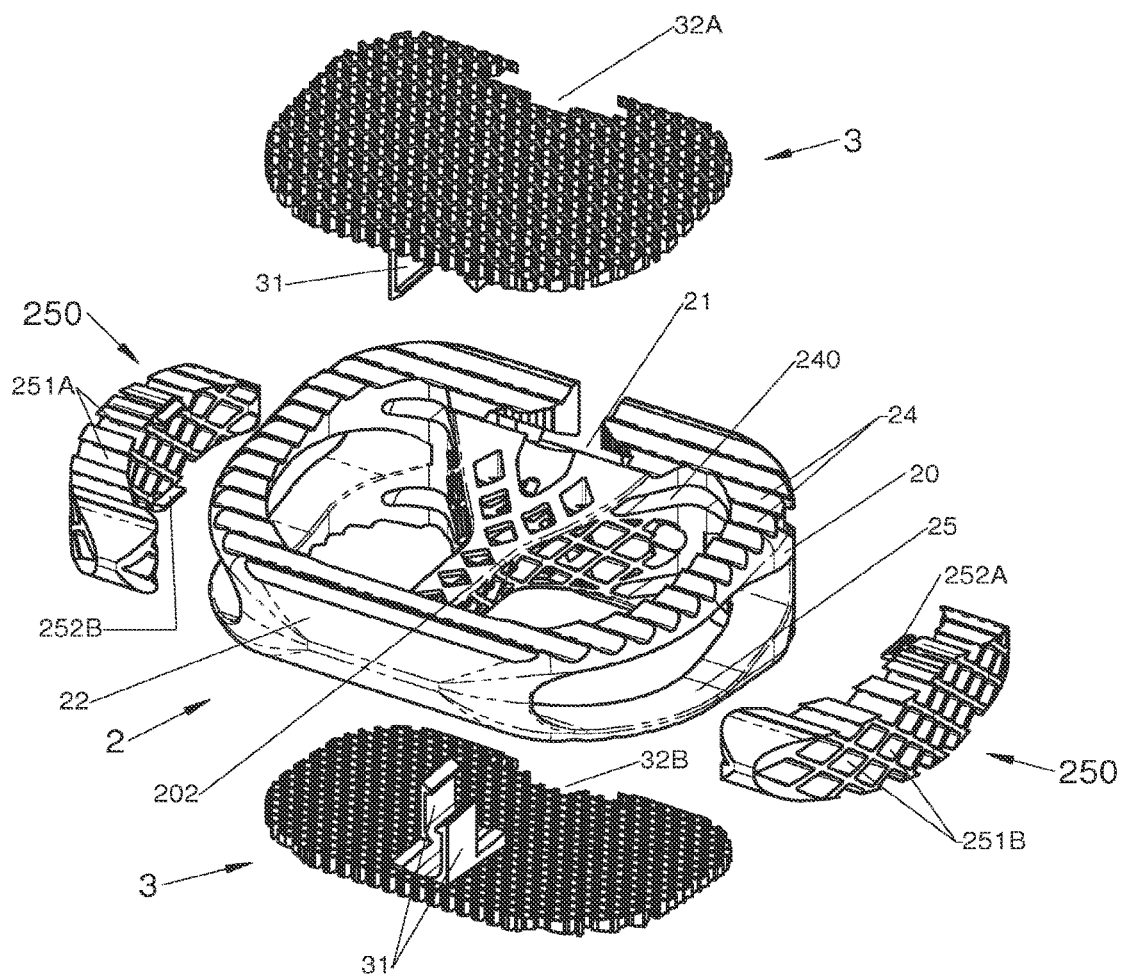
Figure 9B:
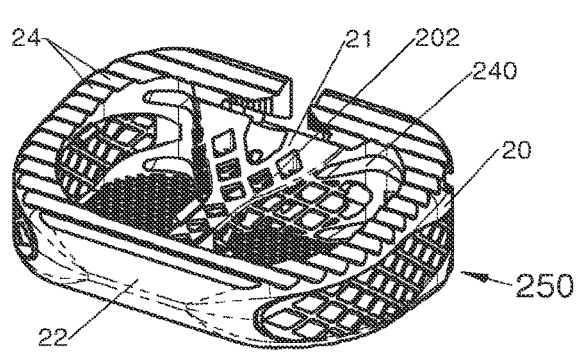
Figure 9C:
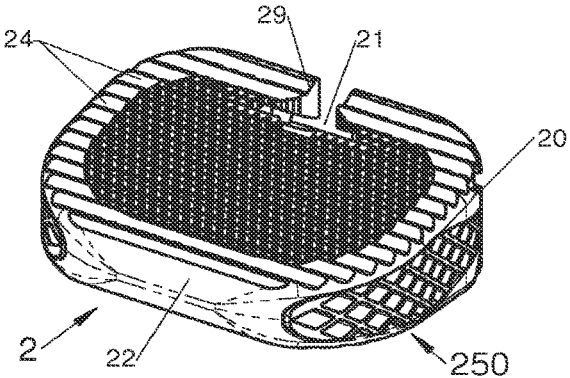
Figure 10A:
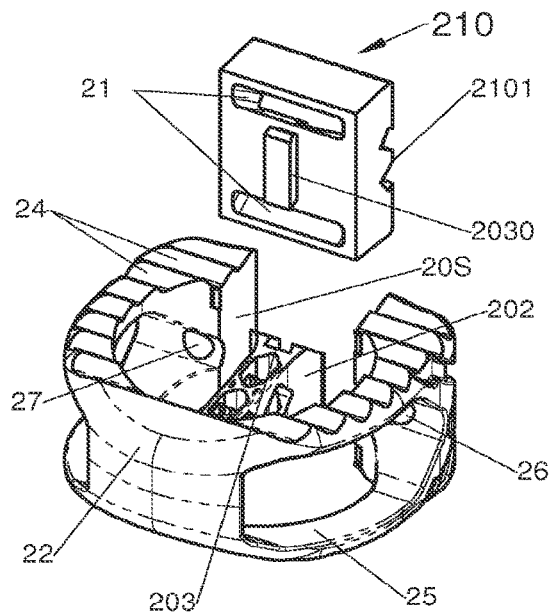
Figure 10B:
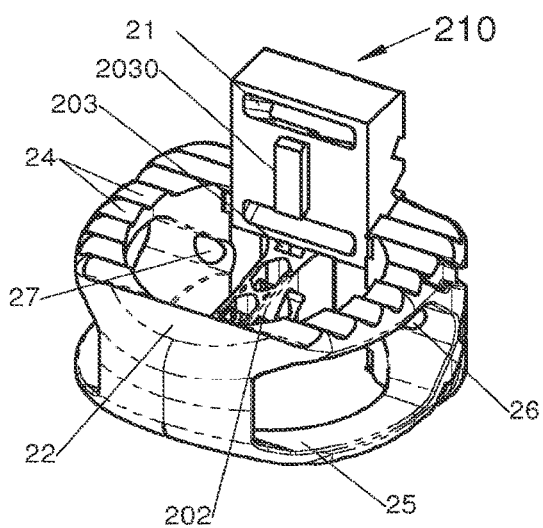
Figure 10C:
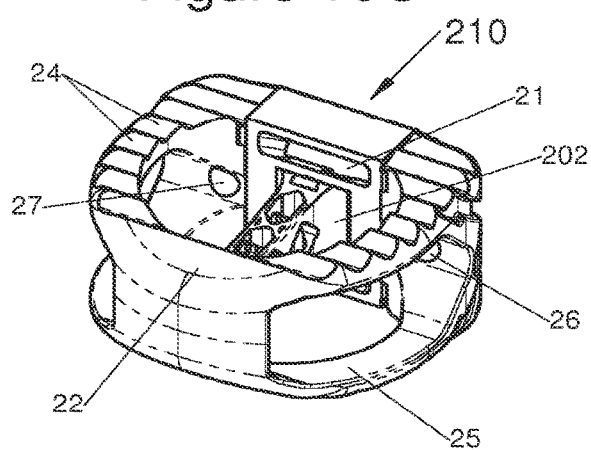
Figure 10D:
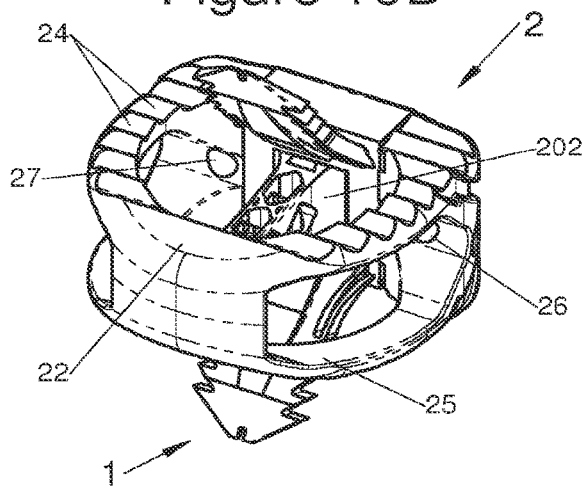
Figure 11A:
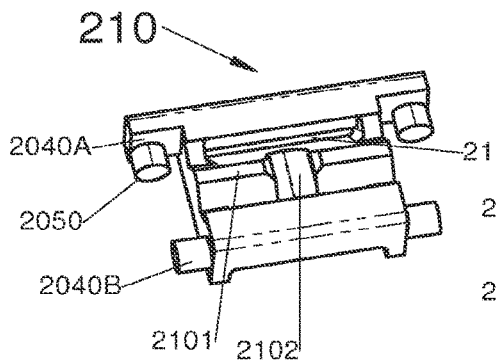
Figure 11B:
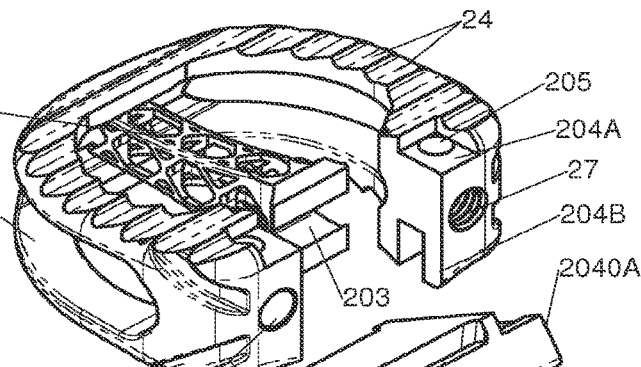
Figure 11C:
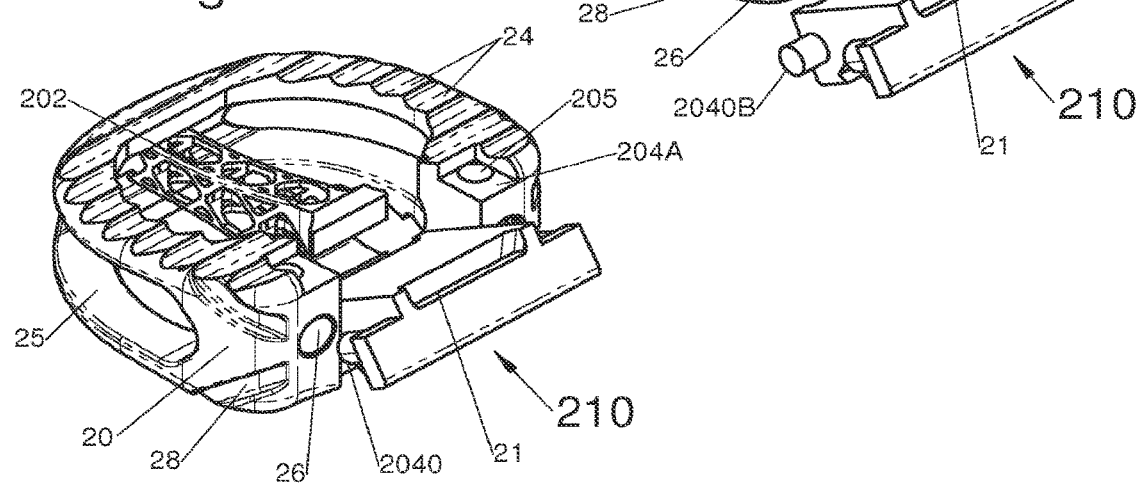
Figure 11D:
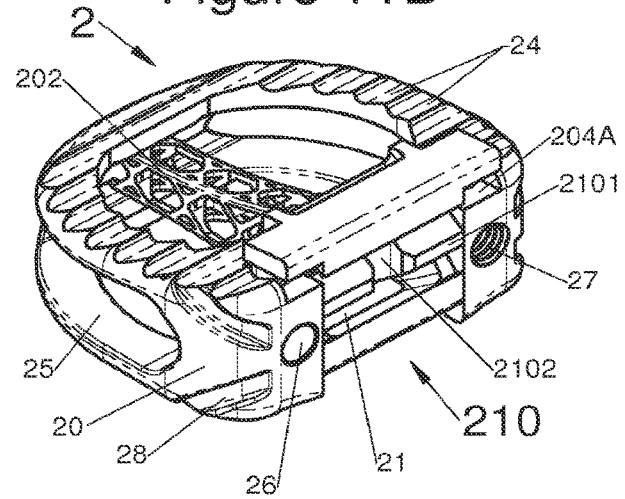
Figure 11E:
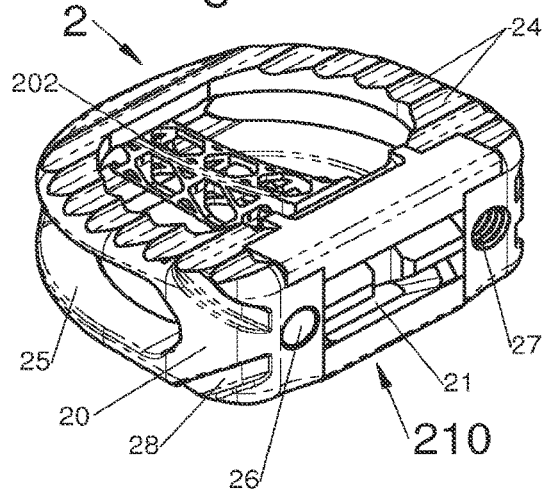
Figure 12A:
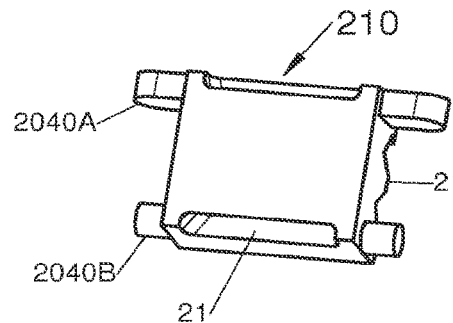
Figure 12B:
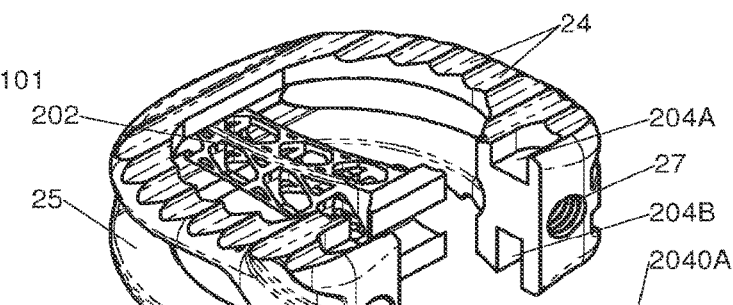
Figure 12C:
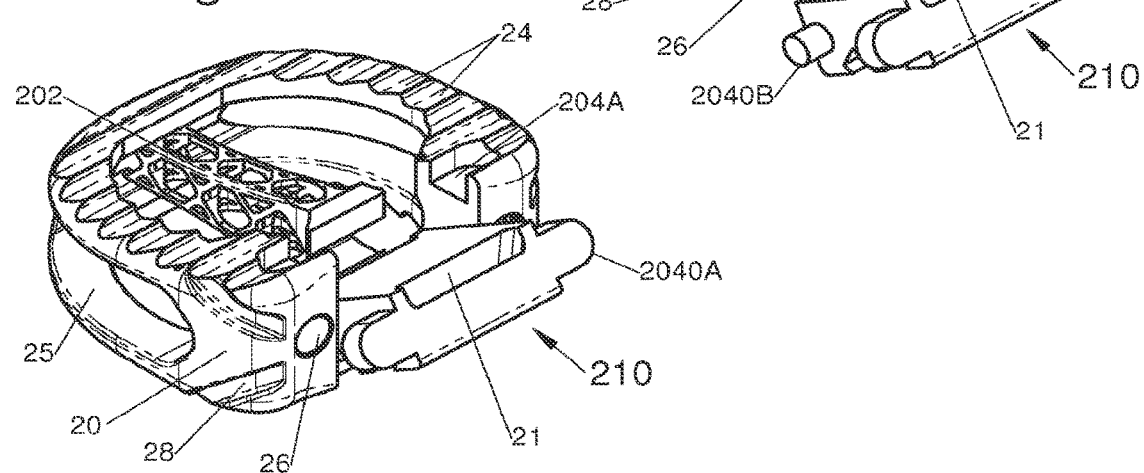
Figure 12D:
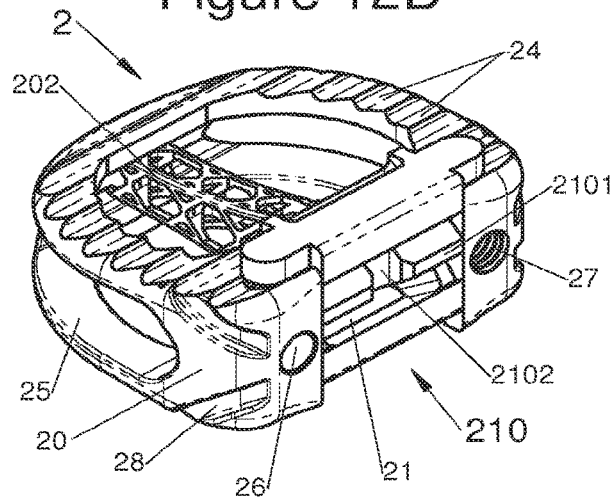
Figure 12E:
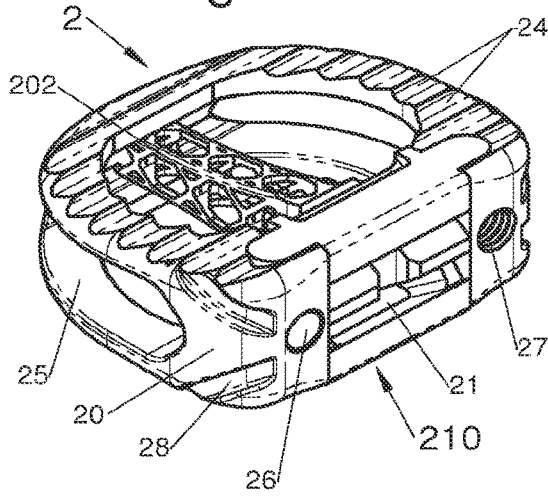
Figure 13A:
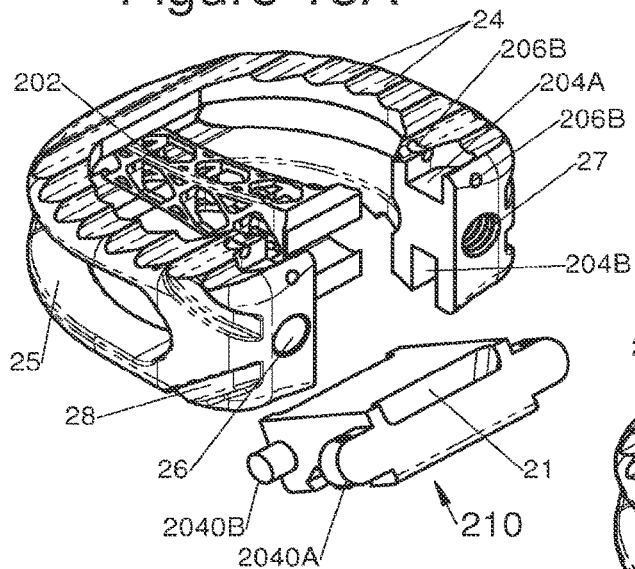
Figure 13B:
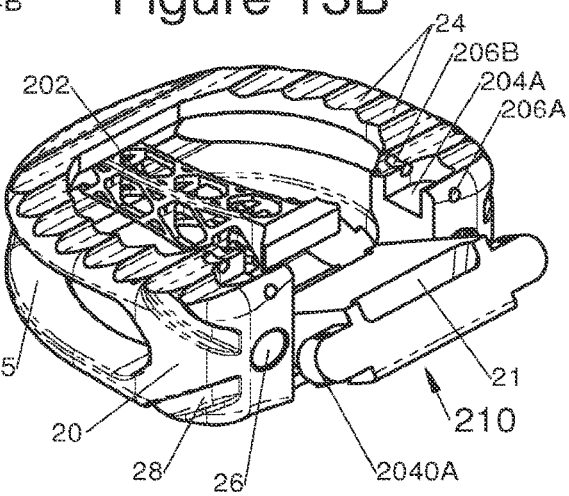
Figure 13C:
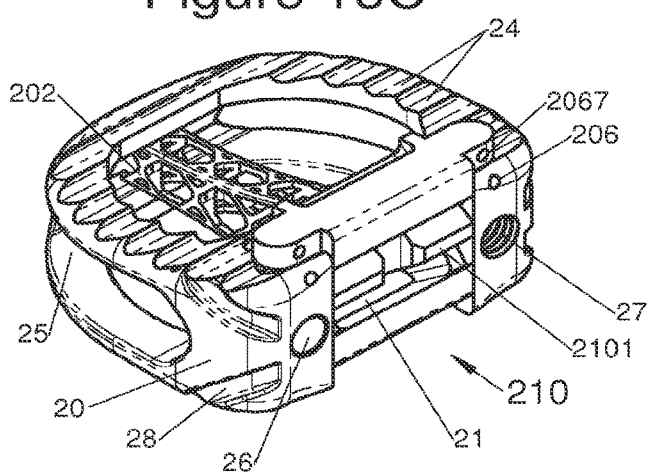
Figure 13D:
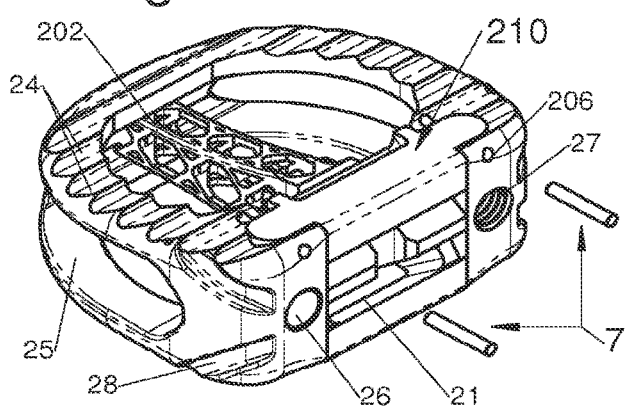
Figure 13E:
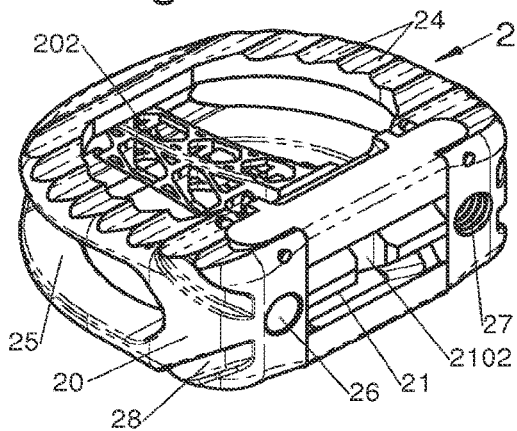
Figure 15A:
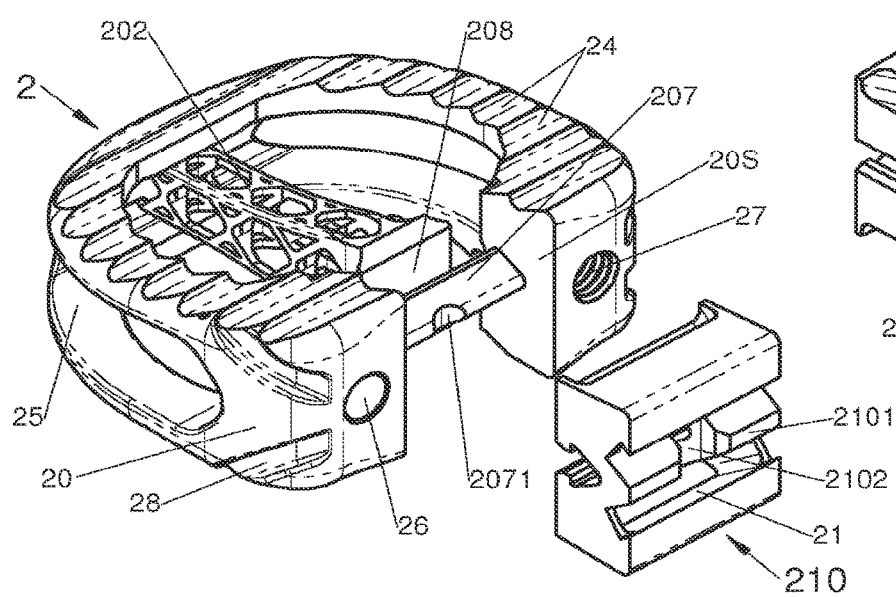
Figure 15B:
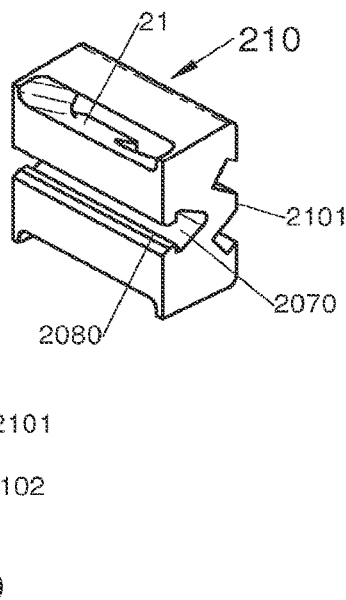
Figure 15C:
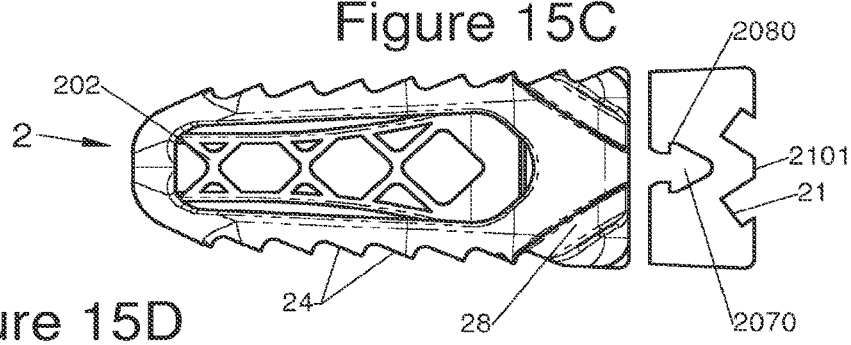
Figure 15D:
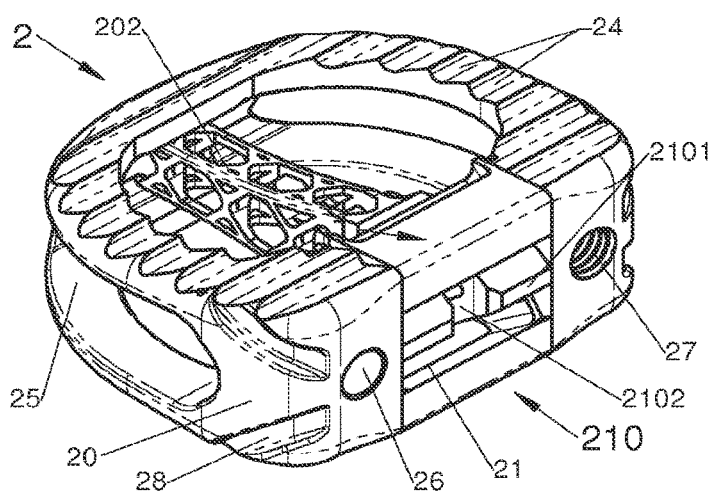
Figure 16A:
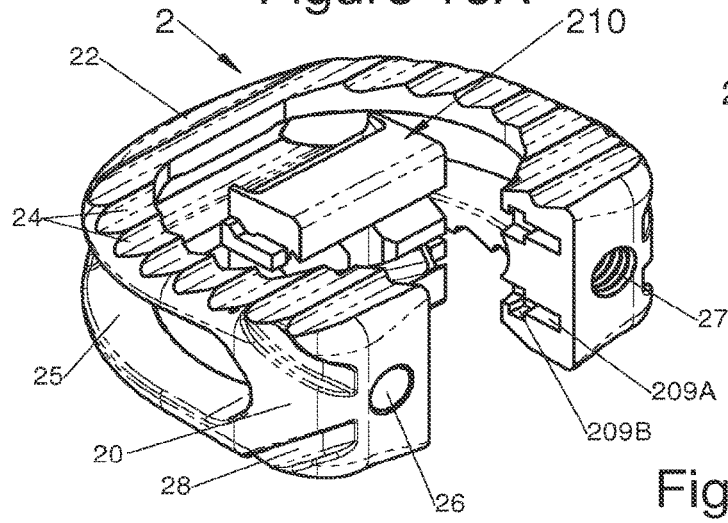
Figure 16B:
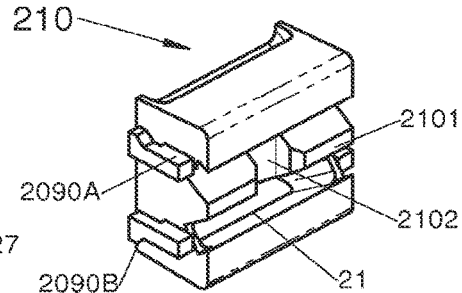
Figure 16C:
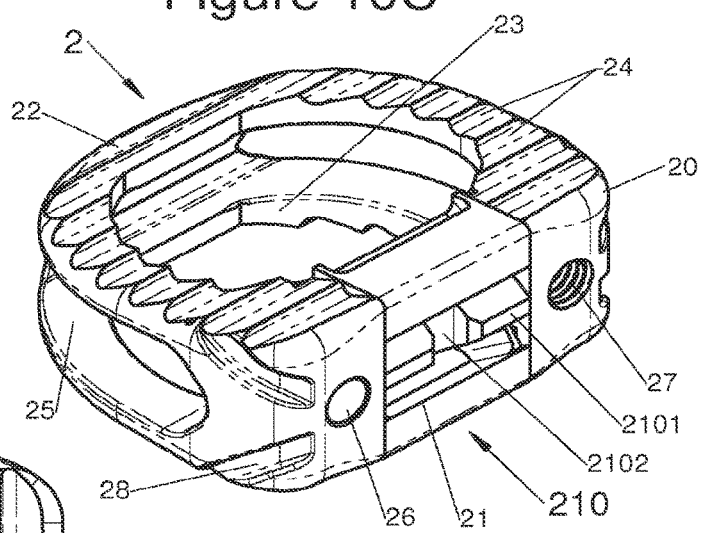
Figure 16D:
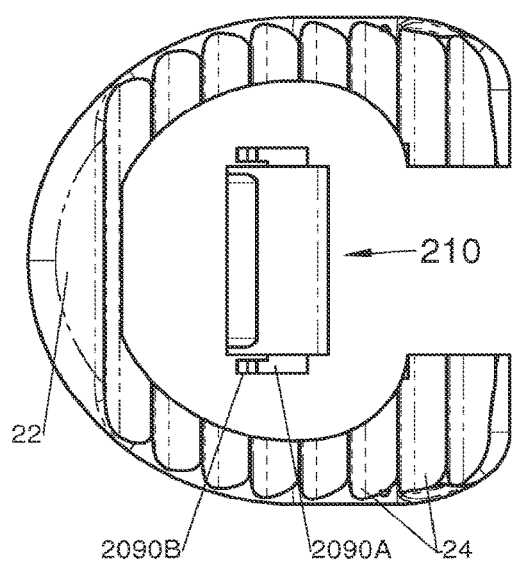
Figure 17A:
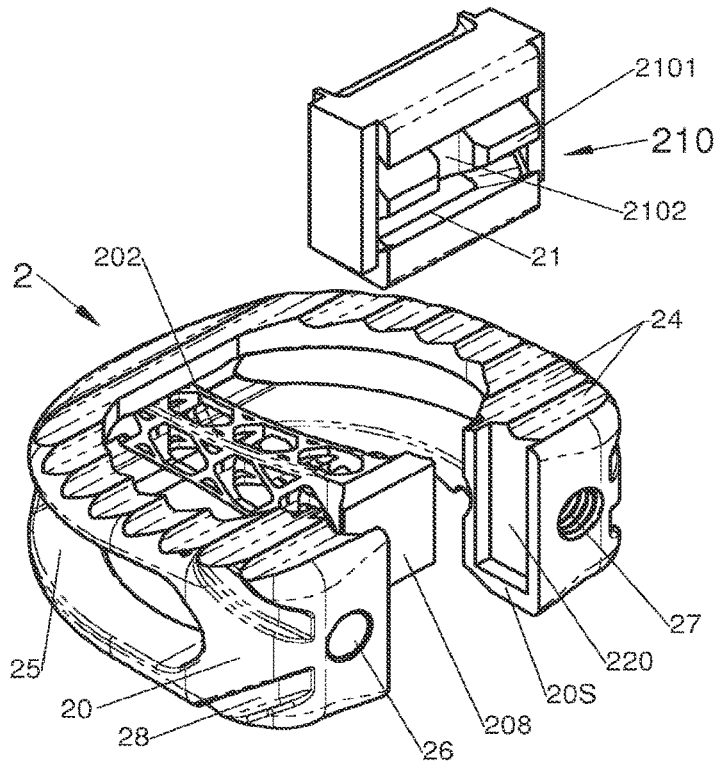
Figure 17B:
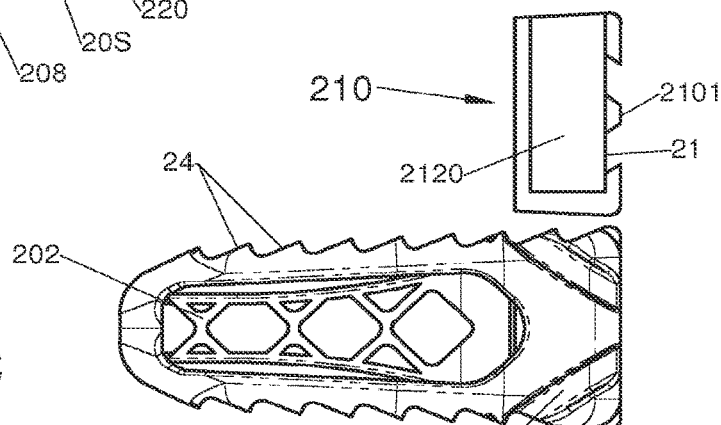
Figure 17C:
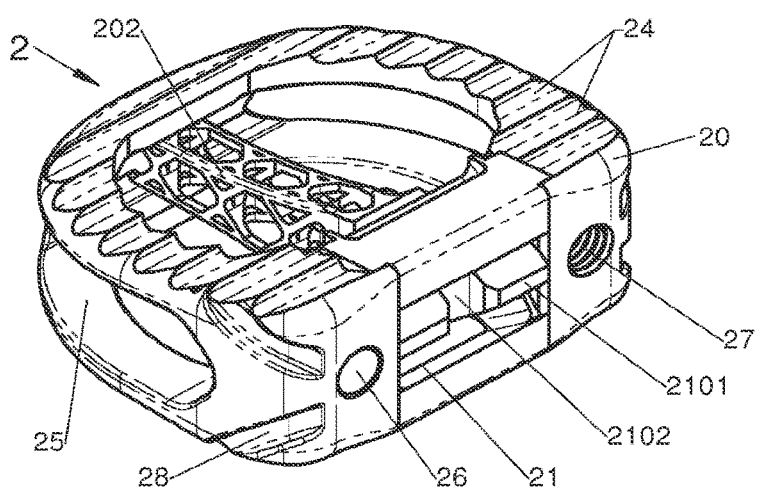
Figure 18A:
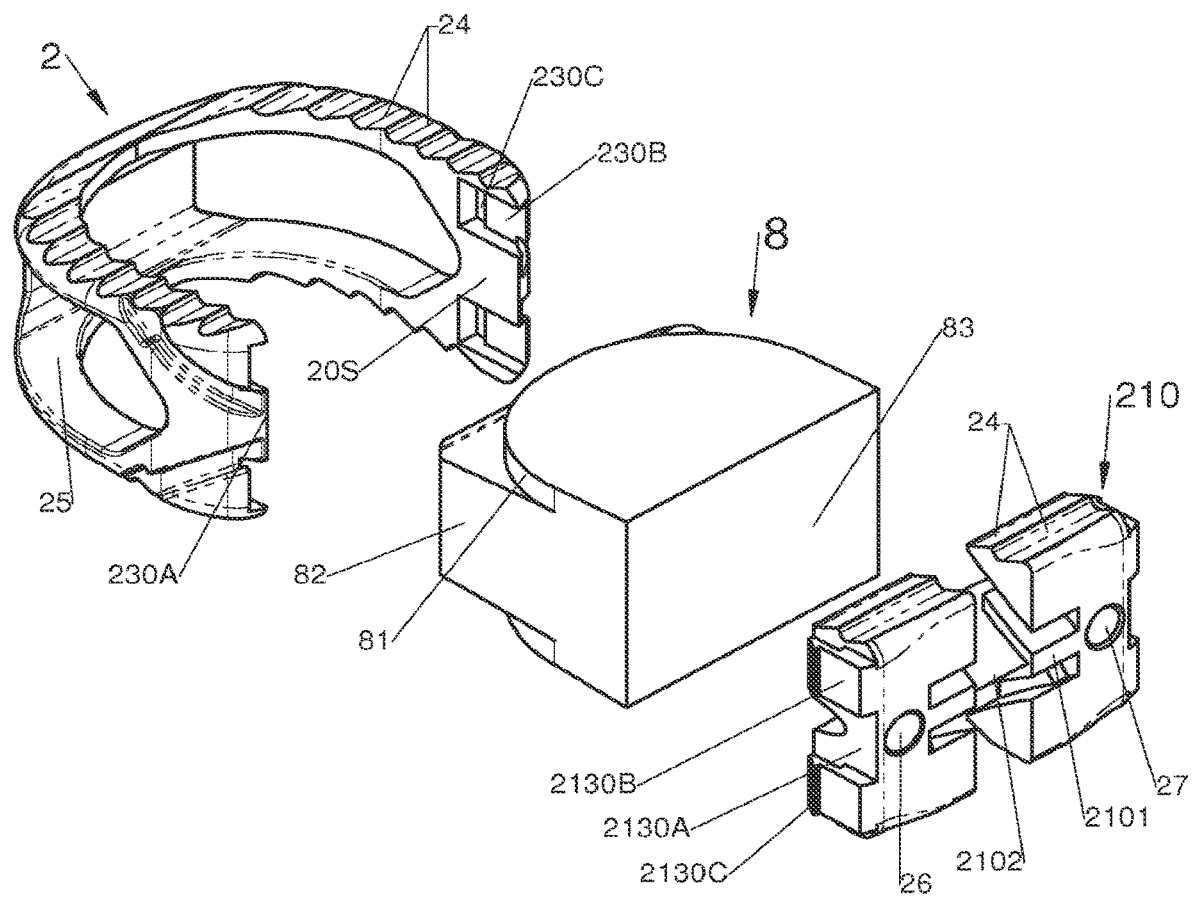
Figure 18B:
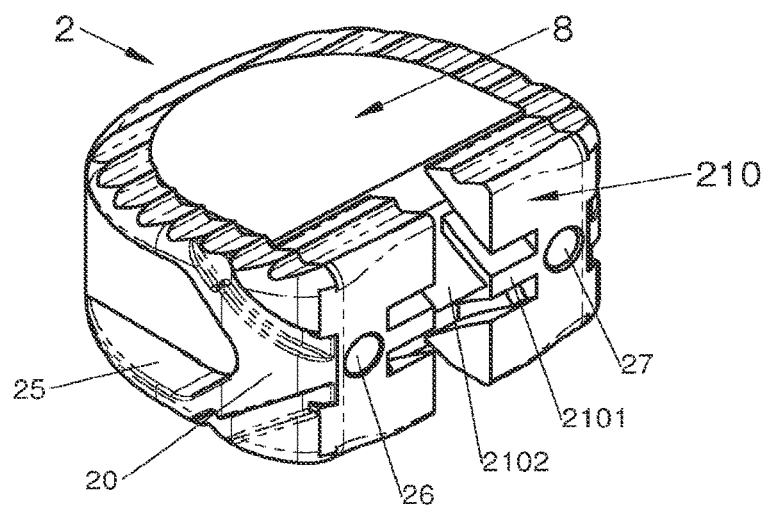
Figure 20A:
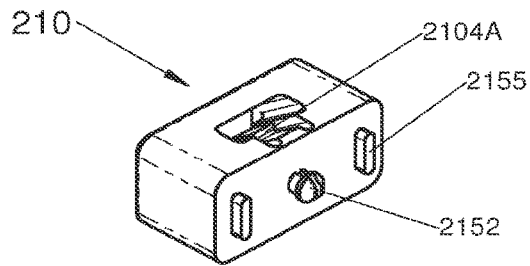
Figure 20B:
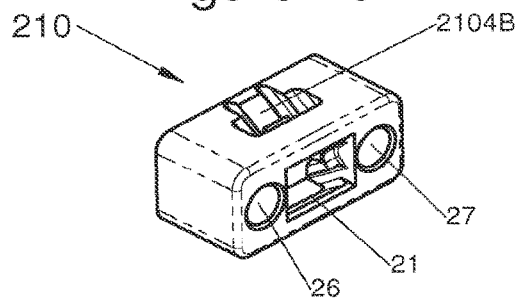
Figure 20C:
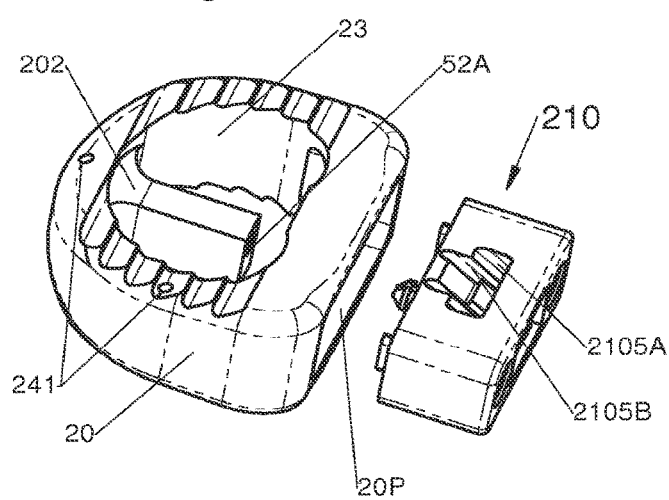
Figure 20D:
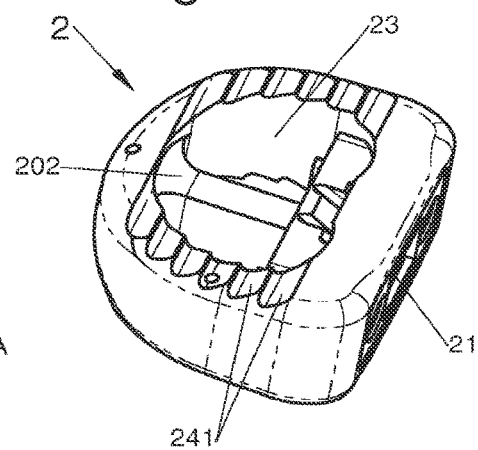
Figure 20E:
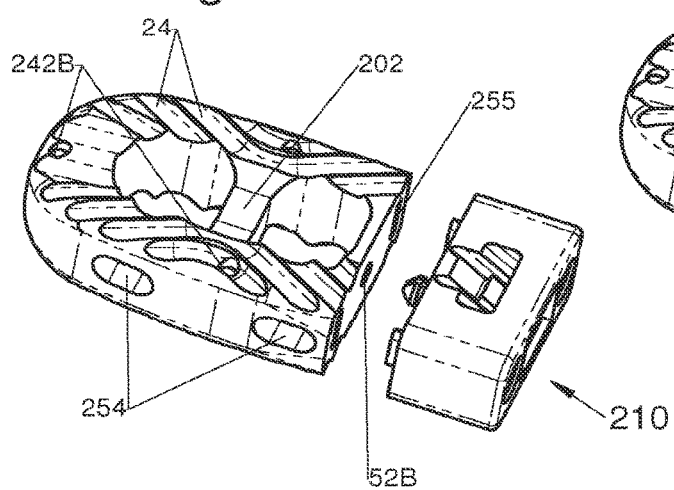
Figure 20F:
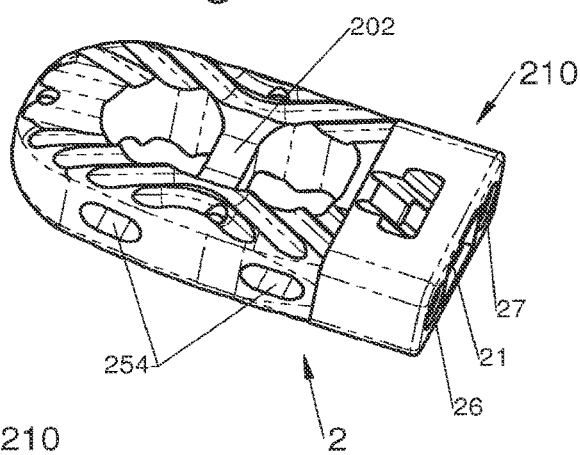
Figure 21A:
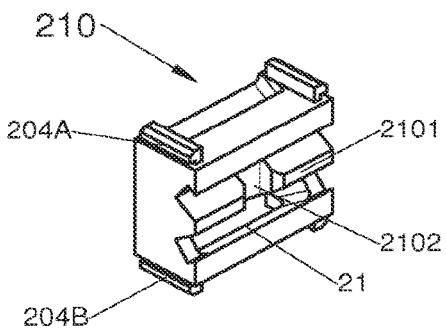
Figure 21B:
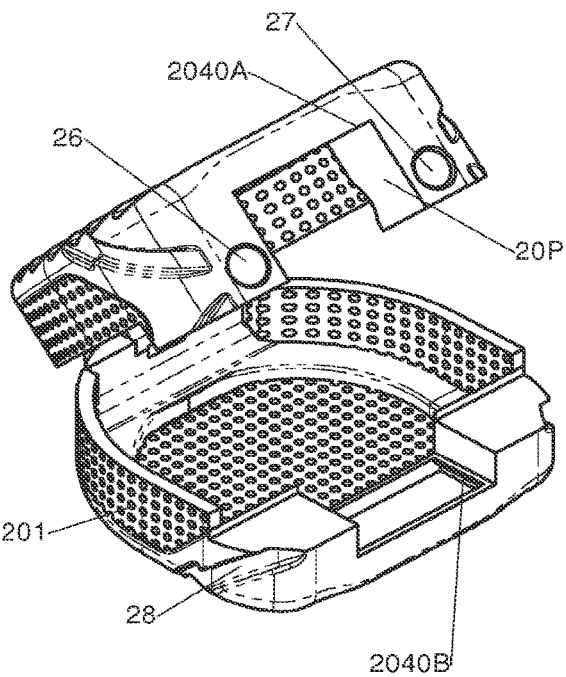
Figure 21C:
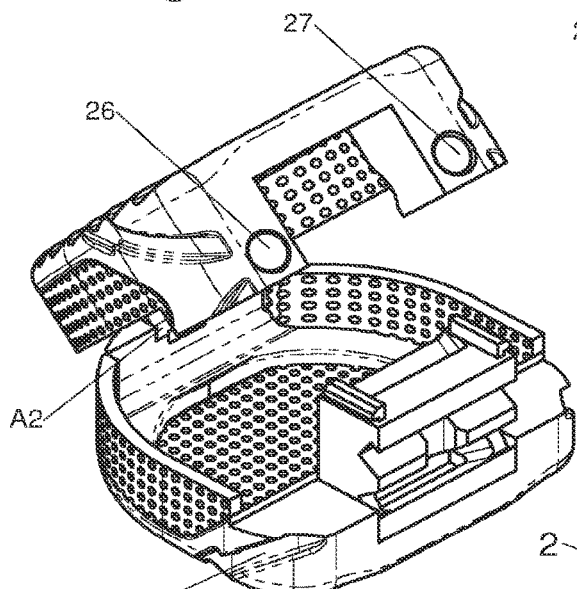
Figure 21D:
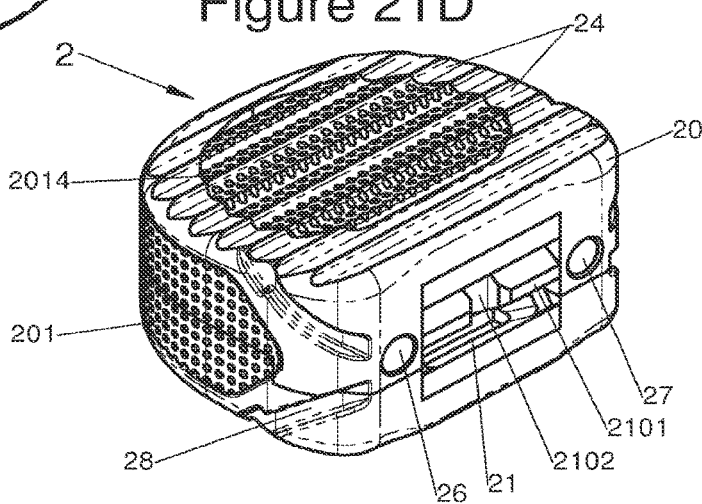
Figure 22A:
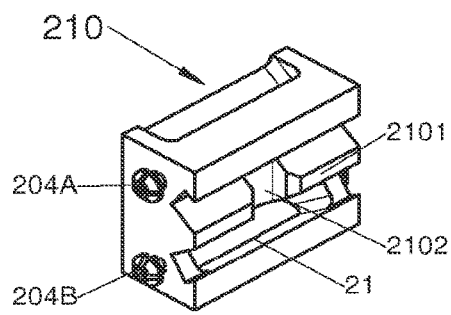
Figure 22B:
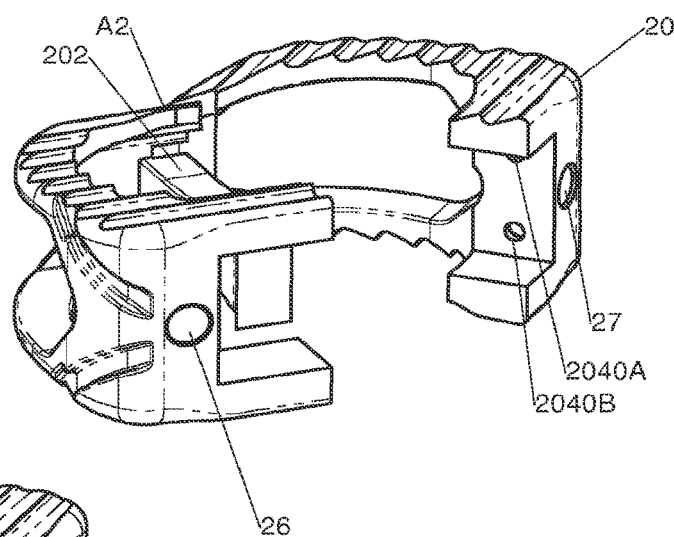
Figure 22C:
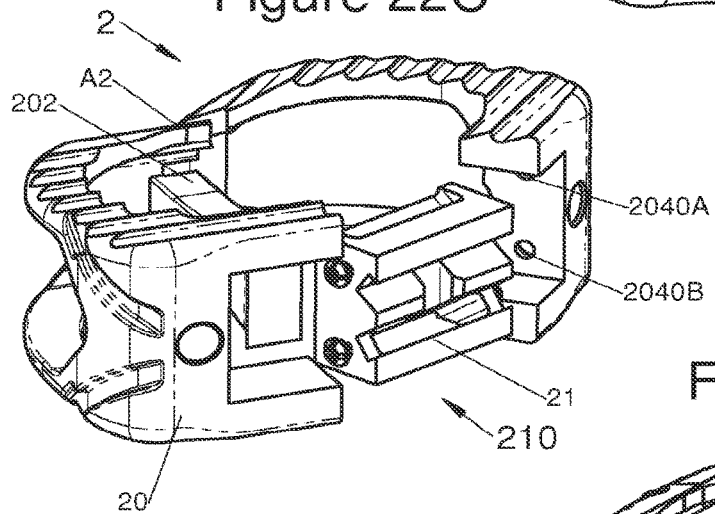
Figure 22D:
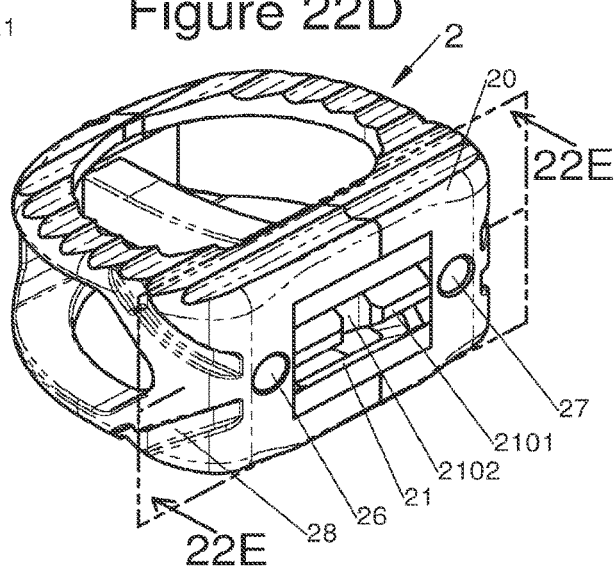
Figure 22E:
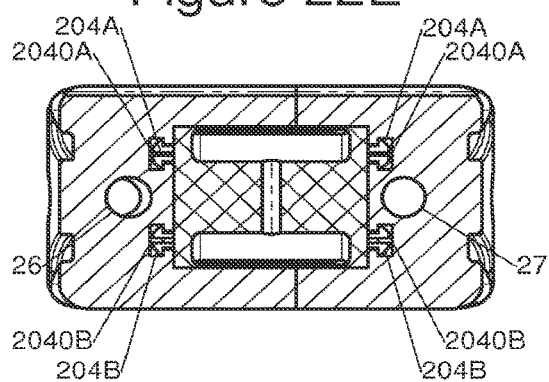

FIG. 5A shows a perspective view of an embodiment of a graft insert and of an intervertebral implant capable of receiving this graft insert, FIG. 5B shows a profile view of this graft insert inserted into this implant, FIGS. 5C and 5D show respectively a profile view and a perspective view of another embodiment of a graft insert and of an intervertebral implant capable of receiving this graft insert;

FIG. 6 shows a perspective view of an embodiment of two graft inserts and of an intervertebral implant capable of receiving these graft inserts;

FIG. 7A shows a perspective view of an embodiment of a graft insert and of an intervertebral implant with reinforcement capable of receiving this graft insert, FIG. 7B shows a perspective view of this intervertebral implant and of graft inserts according to another embodiment;

FIG. 8A shows a bottom view of an embodiment of an intervertebral implant with reinforcement including graft inserts, FIG. 8B shows a perspective view of this intervertebral implant and these graft inserts before assembly;

FIGS. 9A, 9B and 9C show a perspective view of an embodiment of graft inserts and of an intervertebral implant with reinforcement capable of receiving these graft inserts in the upper, lateral, and lower surfaces respectively before, during and after assembly;

FIGS. 10A, 10B and 10C show a perspective view of an embodiment of an anchoring insert and of a reinforced implant with an opening at the rear capable of receiving this anchoring insert, respectively before, during and after assembly and FIG. 10D shows a perspective view of this implant equipped with this insert and with two bone-anchoring devices;

FIG. 11A shows a perspective view of an embodiment of an anchoring insert, and FIGS. 11B, 11C and 11D, and 11E show a perspective view of an embodiment, of this anchoring insert and of an intervertebral implant with reinforcement with an opening at the rear capable of receiving this anchoring insert respectively before insertion, after insertion, after pivoting and after translation of this insert in the rear opening of this implant;

FIG. 12A shows a perspective view of an embodiment of an anchoring insert, and FIGS. 12B, 12C and 12D, and 12E show perspective views of an embodiment of this anchoring insert and of an intervertebral implant with reinforcement with a rear opening capable of receiving this anchoring insert, respectively before insertion, after insertion, after pivoting and after translation of this insert in the rear opening of this implant;

FIGS. 13A, 13B and 13C, 13D and 13E show a perspective view of an embodiment of an anchoring insert and of an intervertebral implant with reinforcement with a rear opening capable of receiving this anchoring insert, respectively before insertion, after insertion, after pivoting, after translation but before locking and after locking of this insert into the rear opening of this implant;

FIGS. 14A, 14B, 14C, 14D and 14E show perspective views of an intervertebral implant with central reinforcement including a posterior insert according to five different embodiments comprising respectively two anchoring devices in the form of plates equipped with lateral withdrawal abutments, two anchoring devices in the form of plates equipped with a central withdrawal abutment, no anchoring device, two L-section anchoring devices and two anchoring devices in the form of slotted point screws;

FIG. 15B shows a perspective view of an embodiment of an anchoring insert, FIGS. 15A and 15D show perspective views of this anchoring insert and of an embodiment of an intervertebral implant with reinforcement with a rear opening capable of receiving this anchoring insert, respectively before and after assembly, and FIG. 15C shows a profile view of this anchoring insert and of this intervertebral implant before assembly;

FIG. 16B shows a perspective view of an embodiment of an anchoring insert, FIGS. 16A and 16C show perspective views of this anchoring insert, and of an embodiment of an intervertebral implant with reinforcement with a rear opening capable of receiving this anchoring insert, respectively before and after assembly, and FIG. 16D shows a top view of this anchoring insert and of this intervertebral implant before assembly;

FIGS. 17A and 17C show perspective views of an embodiment of an anchoring insert and of an intervertebral implant with reinforcement with a rear opening capable of receiving this anchoring insert, respectively before and after assembly, and FIG. 17B shows a profile view of this intervertebral implant before assembly;

FIGS. 18A and 18B show perspective views of an embodiment of an intervertebral implant open at the rear and capable of receiving a graft insert or a graft and an anchoring insert, respectively before and after the insertion of the latter into this implant;

FIGS. 19A and 19B show perspective views of an embodiment of two graft inserts and of an intervertebral implant with central reinforcement with an opening in front capable of receiving these two graft inserts, respectively before and after assembly, and FIGS. 19C and 19D show a profile view of this implant and of these inserts, respectively before and after assembly;

FIGS. 20A and 20B show perspective views respectively in front of and to the rear of an anchoring insert according to one embodiment, FIGS. 20C and 20D show perspective view of an intervertebral implant with reinforcement with a rear passage for receiving the same anchoring insert, respectively before and after assembly, FIGS. 20E and 20F show, according to another embodiment, perspective views of an intervertebral implant with reinforcement with at least one attachment at the rear for receiving this same anchoring insert, respectively before and after attachment of this same anchoring insert to the rear of the implant;

FIGS. 21A and 21B show perspective views of an embodiment, respectively of an anchoring insert and of an intervertebral implant opening by pivoting around a horizontal axis and FIGS. 21C and 21D show perspective views of this insert and this implant, respectively during and after their assembly by closure of the implant;

FIGS. 22A and 22B, 22C and 22D show perspective views of an embodiment of an anchoring insert and of an intervertebral implant opening by pivoting around a vertical axis and FIGS. 22C and 22D and 22E show perspective views of this insert and this implant, respectively during and after their assembly by closure of the implant, FIG. 22E shows a section view along the section plane 22E-22E of FIG. 22D, of this implant closed again with its insert inside its rear portion

DESCRIPTION OF THE PREFERRED EMBODIMENTS OF THE INVENTION

Various embodiments of the present invention relate to a vertebral implant (preferably intervertebral and in particular intersomatic, particularly for an arthrodesis of at least two adjacent vertebrae) and inserts for this implant, but preferably rather a system (e.g. a kit or an assembly) comprising at least one vertebral implant and a plurality of associated inserts (integrable into or associable with or assemblable with) this type of implant. Various embodiments of the present invention therefore relate to a system of vertebral implants and modular inserts comprising at least one bone implant, designed generally to be implanted between two bone structures or inside a cavity in a single bone structure. Various embodiments of the present invention are particularly suited for use in the spine and therefore relate in particular to a vertebral implant, designed for implantation in a vertebral segment composed of at least two vertebrae. This implant is intended to be customizable, modular thanks to various inserts which will be mounted in or on the implant to provide it with means for accomplishing various functions detailed in the present application. Various embodiments therefore relate to a system also comprising inserts for equipping such implants. In particular, this implant could be an implant of the "intervertebral" type implanted between two adjacent vertebrae or an implant of the "corpectomy" type implanted on a segment which can extend beyond a single intervertebral space, or even on several vertebral bodies and/or spaces, but it could also be an implant of the "facet" type implanted between two articular facets or in the sacroiliac joint. In fact, various embodiments relate to implants provided with at least one insert facilitating bone growth and allowing an effective arthrodesis (bone fusion) to be offered in various implantation sites and the examples supplied above should therefore not be considered as limiting. Thus, various embodiments could provide for an implant which is not designed for the spine but rather configured (particularly in terms of three-dimensional shape) for another type of bone of the musculoskeletal system. It will be noted that an insert can facilitate arthrodesis due to the fact that it drives bone growth due to a particular configuration, particularly of shape, (graft insert) but also due to the fact that it attaches and immobilizes (at least partially) the bones that it is is desired to fuse (bone-anchoring insert). On the other hand, the present application describes various embodiments of a bone anchoring for the implant, and therefore details various types of bone-anchoring devices, generally called "anchors" in the present application, even though it can also be a screw implanted by screwing (spiral rotation), as illustrated for example in FIG. 14A, or of a device planted in the bone by following a rectilinear translation or following a curvilinear trajectory, as illustrated for example in FIG. 14A, 14B or 14C. The term anchor is therefore used here only in reference to its anchoring function and it does not imply any limitation of shape or of structure, with the exception of the fact that the anchor is preferably elongated along a longitudinal axis which extends between a first end, designated here as the "anterior end," designed to penetrate into a bone (generally a vertebra) and a second end, designated here as the "posterior end" designed generally to remain in the implant to retain it, to maintain it in place. It will be noted that the designations of the ends, "posterior" and "anterior," of the anchor (1), of the implant (2), or of any other element, are used in the present application with reference to the direction along which the anchor (1) is inserted. Thus, for the anchor (1), the first end, called the anterior end, is that designed to be inserted first and designed to penetrate into a vertebra to attach an implant. Regarding the implant, its wall or its end designated as posterior is that by which it is generally held to be implanted, whether this wall is really posterior to the implant or not during its implantation. In the case of the spinal implants described in the present application, this posterior end can actually be arranged at the rear of the patient or not, particularly for implants which are essentially designed for implantation by a posterior or transforaminal route. Consequently, the terms "anterior" and "posterior" are not designed to refer simply to the patient or to one of his anatomical characteristics, but to the direction of insertion of the anchor into the implant and/or the implant itself (whether this implant is itself implanted along an antero-posterior axis or not). On the other hand, the terms "height" and "thickness" generally designate the dimensions of the elements in an orientation parallel to the axis of the spine (once implanted in it) and the terms "upper" and "lower" (or above and below) are generally also defined according to this orientation (vertical when the patient is standing), with no limiting implication for the invention. Likewise, the terms "vertical" and "horizontal" are used in a non-limiting manner with reference to the axis of the spine, considering the patient to be standing and the implant positioned in the spine. On the other hand, the terms "width" and "length" designate dimensions in a plane perpendicular to the axis of the spine (a transverse plane), with the width generally being in the mediolateral direction while the length will be in the anteroposterior direction, with this definition not having the slightest limiting implication for the invention. It will also be noted that reference is made here to a longitudinal axis between two ends and that this longitudinal axis corresponds possibly to an anteroposterior axis of the anchor (1), but that this axis is generally oriented obliquely with respect to the implant because the anchor is often inserted from the periphery of the spine into a vertebral structure (usually a vertebral body and generally into a vertebral end-plate). Moreover, this axis of the anchor follows the same curved trajectory in numerous embodiments and it is in fact, on the one hand, parallel to a tangent of the arc described by the anchor and, on the other hand, therefore designated as anteroposterior with respect to the ends of the anchor rather than with reference to the spine. Likewise, the axis of the passage is designated using the same reference even though it is oblique and though it can be curvilinear or rectilinear. It will also be noted that the term "substantially" is regularly used in the present description, particularly regarding a feature such as an orientation or a direction, so as to indicate that the feature in question can in fact be slightly different and not be exactly as designated (for example, the expression "substantially perpendicular" can be interpreted as "at least approximately perpendicular" because it can be possible to select an orientation which is not exactly perpendicular so as to be able to nevertheless accomplish substantially the same function). Moreover, terms such as the term "substantially" used in the present application can also be interpreted as defining that the technical feature can be "in general" ("generally") and often "preferably" as indicated, but that other embodiments or configurations can be within reach of the present invention. The different elements comprising the system of modular implants and inserts will now be described, with reference to the figures but in a non-limiting manner. In fact, the system, but also the implants and/or inserts can individually take on particular technical features which it is appropriate to examine individually without limiting them to other features, although various embodiments of the present invention relate more particularly to the advantageous combinations provided by association, or even the synergy of the various implants and inserts described in the present application.

Preferably, the vertebral implant (2) includes, generally, a body (20) the walls whereof delimit a cavity (23) leading to the outside of the body (20) through at least one opening in at least one of said walls. In particular, the body could include one or more openings, preferably several so that the cavity leads to several faces of the implant which is thus open from one side to the other, which will allow the bone to colonize completely. Thus, the body can include at least one lateral opening and/or at least one posterior opening and/or at least one anterior opening and, of course, at least one upper and/or lower opening as is often observed in the prior art. Moreover, in the case of an implant (2) having at least one cavity (23) for example, as can be seen particularly in certain embodiments shown in FIGS. 20E, 20F and 21B, holes (201, 254) can be provided in at least one of the walls of the implant (the lateral walls in the examples shown), so as to also allow the growth of bone tissue transversely to the disc space (i.e. through the implant, parallel to the vertebral end-plates).

Moreover, the implant (2) preferably includes at least one passage (21) passing through the implant (2) from the periphery (a lateral or anterior or posterior surface) toward an upper or lower surface for receiving a bone-anchoring device (1) capable of anchoring the implant (2) in at least one of said vertebrae. On the other hand, the system includes at least one implant (2) which includes at least one insert from among the following two types of inserts, but which is preferably combined with a plurality of graft inserts and/or bone-anchoring inserts selected from among at least one of the following types of inserts:

at least one graft insert (3, 3A, 3B, 4, 5A, 5B, 6A, 6B, 6C, 6D, 202, 250) capable of being colonized by bone tissue and/or receiving at least one bone tissue graft and/or at least one substitute;

at least one bone-anchoring insert (210) comprising said passage (21) capable of receiving said bone-anchoring device (1).

Various embodiments therefore relate to an implant the walls whereof define a sort of skeleton generally capable of supporting at least partially the forces exerted on the implant, particularly for maintaining or restoring a distance (often a height) between two bone structures (vertebrae for example). Moreover, this skeleton delimits and interior cavity capable of receiving various types of interchangeable and not mutually exclusive inserts, depending on the needs of the patient or the desires of the surgeon. In particular, certain inserts, called here graft inserts, could serve as an accommodation structure for bone growth and other inserts, called here attachment inserts, could serve for accommodating the anchoring of the implant in the vertebrae. In fact, various graft inserts, hollow, solid, meshed, lattice or not could be used to fill the cavity at least partially. Various embodiments of these graft inserts will be capable of being colonized by the bone tissue of the patient and/or receiving a graft and/or a substitute, for example to accelerate and/or favor bone growth. These inserts can in particular have as aims that the fusion occurs for example between 2 vertebrae, but also favoring the attachment of the implant on the bone, for example on the vertebral end-plates, or even forming a surface, at least upper or possibly lower, limiting the risks of sinking the implant into the bone, in particular the adjacent vertebral bodies. It will be noted that the terms "be colonized" and "graft and/or substitute" also include the known possibilities of different combinations of substances promoting bone growth, such as an autologous graft or as in particular growth factors or any type of favorable chemical composition. Thus the fact that the graft insert allows bone growth will sometimes be taken advantage of by facilitating its colonization by the surrounding bone tissue, for example by its geometry and/or its mesh structure and/or its composition. This possibility of allowing the graft insert to allow itself to be colonized, without adding bone grafts, can prove particularly advantageous, particularly for the patient, if only for example because it allows avoiding or limiting the removal of bone from the patient, which is often painful, in particular in the iliac crest. It will also be noted that the present application designates by the term "insert" any device, element or structure which is in fact insertable inside the implant (possibly while flush with or projecting beyond the perimeter), and insofar as several inserts can be introduced instead of each other or in a mutually complementary manner, that these inserts can be attached in the implant or not and that they can be withdrawn from it or not. Moreover, in certain embodiments, the implant is in fact open on one of its faces and its cavity therefore leads to the periphery of the implant. Thus at least one of the inserts, preferably (but not solely) a bone-anchoring insert, can in fact be added to the implant to form one of its walls, as shown in FIGS. 7B, 9B, 10B, 11C, 12C, 13C, 15D, 16C, 17C, 18B, or 20C and 20D for example. In certain embodiments, it is even possible that at least one of the inserts is not really introduced inside the implant, i.e. inside the cavity, but could in fact be coupled to the perimeter of the implant, to one face (generally posterior) at least, as shown in FIGS. 20E and 20F for example. This type of configuration sometimes allows adding an insert to an implant, particularly during implantation, but it is generally preferred that the insert be really inside the zone defined by the walls of the body so that the reliability of the assembly does not risk being weakened by the coupling means between a coupled insert and an implant, to limit the risks that the latter may become detached. It will also be noted that the present application refers to bone grafts or substitutes and that these terms should also be interpreted as designating in fact any type of material or composition allowing bone growth, which can be optimized or controlled, without any limitation. It is known for example in the prior art to use various types of grafts or substitutes, such as autologous bone grafts for example (i.e. derived from a withdrawal from the patient himself), possibly with a preliminary treatment, particularly crushing, or bovine bone grafts the structure whereof is near that of human bone, but also substitutes such as β-tricalcium phosphate (β-TCP), the composition whereof, very close to the mineral component of bone, is perfectly biocompatible and bioactivity whereof allows total resorption and optimal bone regrowth in a few months, or even hydroxyapatite (HAP), the composition whereof is also very close to the mineral composition of bone and therefore also biocompatible, but the resorption whereof will generally be slower. Thus, the term "graft" is generally used in the present application to designate both autologous bone tissue and a substitute or any other grafting substance or any type of compound or chemical composition.

On the other hand, it is understood that various embodiments allow the costs of manufacture and of stock management to be limited while still supplying a highly varied range of implants that the surgeon can adapt as he sees fit. In fact, instead of providing an implant for each type of content desired, various embodiments of the invention allow only a common skeleton to be provided in which various types of inserts are adapted, for example depending on the bone growth characteristics desired or depending on the bone-anchoring types desired or even on the desired X-ray transparency of the implant. For example, the surgeon may desire in particular an implant which is very resistant to compression at least in certain directions (as shown for example in FIGS. 5A, 5B, 5C, 5D, 6A, 7B, 8B) and/or which is very favorable to rapid bone growth (as shown for example in FIG. 4D or 9A among others) and/or which has low-invasiveness, or very deep on the contrary, anchoring or even compressive anchoring (as shown for example in FIGS. 14A, 14B, 14C, 14D and 14E). The modularity of the implants of the present application make it possible to respond effectively to the great diversity of desirable technical features for an implant and the figures show illustrative non-limiting and non-mutually-exclusive examples, for the most part. It is therefore understood that various embodiments could deal with assemblies formed from an implant forming the skeleton as described and with a combination of different graft inserts and/or bone-anchoring inserts. In fact, a common basis is formed by the hollow implant and various "accessory" inserts can be added to it. As regards graft inserts in particular, the description hereafter details solid, hollow and meshed inserts which will be used alone or in combination with others to respond to the requirements of the anatomical structures of the patient and the needs of the surgeon.

Various embodiments relate at least to an insert for at least one implant for the implementation of the invention. Thus, certain of these embodiments relate to a graft insert, supplied alone for example, configured for its use in an implant as described in the present application. In fact, it is possible to propose a multitude of inserts which will be capable of being inserted into an implant of the type of those in the present application, particularly integrated with coupling means or not. It is therefore important that it be understood that the scope of the present application can extend to one insert alone, as long as it is provided for its integration in an implant of the type of those of the present application. The same is naturally true with at least one bone-anchoring insert, as long as it is configured for its use in an implant such as those of the present application. The same is true for any combination of these inserts together.

Moreover, the various components of the system of implants (body of the implant, reinforcement, insert, anchors), used in various embodiments, are sometimes based on the use of additive manufacturing techniques (three-dimensional printing or 3D printing), but the scope of the present application is not limited to this technique. In fact, it is more and more frequent today to use this type of technique for the manufacturing of implants. In particular, the present application refers to inserts with a meshed structure (often called "lattice") which in fact are elements of varied shapes (polyhedral and/or rounded for example), the body whereof is not solid but composed of a network of meshes, with variable geometries which in addition have the advantage of generally favoring bone growth and/or allowing good visibility of this bone growth after surgery by imagery methods and/or adding a surface limiting the risks of sinking the implant and/or adding back a surface for attaching the implant on the bone surface, etc. Additive fabrication techniques are particularly useful for this type of meshed structure, and therefore preferentially used for these elements, but also possibly for bone-anchoring or for the body of the implant forming the skeleton receiving these elements for example. Nevertheless, these techniques often involve a certain inaccuracy which is often acceptable for elements such as the inserts and the body, but this inaccuracy is more problematic in the case of an element which requires a more precise adjustment, such as for example the bone anchors which must cooperate with portions that retain the anchors with respect to the implant and which therefore retain the implant in place in or against the bone tissue. Moreover, it is very probable that these additive manufacturing techniques will be improved and improve their tolerances rapidly, so as to offer even more advantages. It could therefore sometimes be preferable to use either machining techniques or more conventional molding, or additive manufacturing techniques for the various elements of the implant and/or insert and/or anchor, particularly depending on the tolerances of these elements and the quality achieved by these various techniques. Thus, the fact of proposing modular implants (e.g. comprising modules that can be assembled with one another, such as a body and inserts), makes it possible to take advantage of the various manufacturing techniques for the various elements. Thus for example it would be possible to provide a meshed insert in additive manufacturing, but a machined or molded anchoring insert with an anchor or a screw, also machined or molded, all assembled with a body obtained by machining or molding or additive manufacturing. Likewise, the use of a meshed insert, particularly filled with a graft, separately from the body of the implant (skeleton) can bring various non-negligible advantages. For example, one advantage relates to obtaining complex shapes for the insert, particularly shapes which would be inaccessible and therefore impossible to obtain by machining, though they can be by additive manufacturing and/or by the fact that the insert can be separately machined. Another advantage relates for example to the possibility of more homogeneous filling of the graft insert by a substance favoring bone growth, for example by soaking it in this substance, or by injecting this substance when a vacuum is formed around the insert, or even by printing this substance inside the insert, or even by preparing the insert with stem cells in an organized manner within the network, or by accomplishing cell culture there.

On the other hand, the various elements in the present application can be manufactured of PEEK (polyetheretherketone) in particular, which have an elasticity similar to cortical bone known from the prior art and/or of titanium and/or of various biocompatible materials or alloys usable with the manufacturing techniques mentioned above. One illustrative and non-limiting example of an advantageous combination of materials includes, on the one hand, a body made of machined or molded PEEK which would allow resisting in an optimal manner the in vivo forces with a module having an elasticity close to that of bone and therefore limiting the forces at the bone/implant interface and, on the other hand, a graft insert with a meshed structure made of titanium which would allow the accommodation of a grafting substance (graft or substitute or substance guiding or stimulating growth). The anchors could then either pass directly through the implant, or through an anchoring insert. If the body of the implant is made of titanium, it is generally preferred that it be much more hollowed out than if it were made of PEEK, given the superior mechanical characteristics of titanium, which makes it possible to leave more space for the graft and also to reduce the "stiffness" of the body which would be too great with titanium (with respect to contact with the bone). Moreover, an implant body made of PEEK or of titanium makes it possible to accommodate various types of graft inserts and the same graft insert is modular to a body regardless of its material as long as the complementarities of shapes and configuration are provided for as described in the present application.

In certain embodiments, the vertebral implant (2) includes at least one bone-anchoring insert (210), but said cavity (23) is configured to receive directly a bone tissue graft or a substitute, without a graft insert (3, 3A, 3B, 4, 5B, 6A, 6B, 6C, 6D, 202, 250). Thus, certain embodiments can deal with an implant including only a bone-anchoring insert for receiving the anchorages and attaching the implant which moreover is configured to receive graft or substitute directly in its cavity, as already known for example in the prior art. Thus such an implant has a cavity which does not necessarily comprise means (openings, locks, etc.) capable of cooperating with graft inserts, but includes at least one anchoring insert such as those described in the present application, which have various advantage and therefore respond to various problems within the field, particularly the modularity of the type of bone-anchoring which is desired by the surgeon, as illustrated for example in FIGS. 14A, 14B, 14C, 14D and 14E.

On the contrary, in certain embodiments, the vertebral implant (2) includes at least one graft insert (3, 3A, 3B, 4, 5A, 5B, 6A, 6B, 6C, 6D, 8, 202, 250), but said passage (21) is provided directly in at least one of said walls of the body (20) without requiring a bone-anchoring insert (210). Thus, the body (20) comprises at least one portion, generally posterior, which includes at least one passage (21) for a bone anchor. The figures of plates 1 to 9 and 19 show illustrative and non-limiting examples of such implants in which a bone anchoring is provided directly in the walls of the body. In these embodiments, a passage (21) is provided directly in at least one wall of the body (20), generally the posterior wall because the anchor can be inserted there. The figures of plates 10 to 18 and 20 to 22 show, on the other hand, non-limiting examples of implants intended for anchoring via an anchoring insert.

On the other hand, of course various embodiments combine the two types of inserts, for the graft and for anchoring. Moreover, in various embodiments, anchoring can be accomplished at least using an anchoring insert, but it is possible to have a supplementary anchoring directly via a passage in a wall of the implant, in addition to this anchoring via an anchoring insert. Likewise, it is clear that the implant can comprises both a graft insert to receive a graft and at least one cavity (or a portion of a cavity) receiving the graft directly without requiring a specific insert. Moreover, each of the illustrative and non-limiting examples described hereafter relate to graft inserts and the anchoring inserts can of course be combined together, unless the contrary is explicitly stated or apparent to a person skilled in the art. Likewise, generally, it will be understood upon reading the present application that each of the technical features of each element, described in at least one embodiment or a configuration, could be isolated from the other features of the object in question (or from the objects in question and/or associated) by said embodiment or said configuration (and therefore relating to the same element or a different element) and/or could be combined with any other technical feature described here, in various embodiments or configurations, unless the contrary is explicitly stated, or these features are mutually incompatible and/or their combination is inoperable, in particular because the structural adaptations which can be required by such isolations or combinations of features are directly derivable from the appreciation of the functional considerations provided in the present application.

On the other hand, modularity is generally provided for due to the fact that the implant is arranged to receive several different types of implants, but it is clear that the reciprocal is possible because various types of implants are generally provided for all the same, if only for various surgical approach paths (anterior, lateral, posterior, transforaminal).

Thus, various embodiments intend that the same insert be usable for several implants and even via different assembly and/or coupling and/or locking means. FIGS. 20C and 20E show particularly pertinent examples of this modularity because the implant, for example anterior or lateral, of FIG. 20C receives the same is attachment insert as the implant, for example posterior or transforaminal, of FIG. 20C, while still possibly using a different coupling mechanism because FIG. 20D shows that the same insert can be introduced into the implant of FIG. 20C, but only conjoined to another implant in FIG. 20E. This example therefore demonstrates the variety of couplings which are made possible by different embodiments.

In certain embodiments, the graft insert (3, 3A, 3B, 4, 5B, 6A, 6B, 6C, 6D, 8, 202, 250) includes at least one of the following elements:
 a meshed modular element (3, 3A, 3B, 6C, 6D);
 a solid modular element (4, 5A, 5B, 6A, 6B, 8), which can in fact sometimes be a graft or substitute or a grafting substance;
 a loading element, called a cassette (6A), capable of receiving at least one such meshed (3, 3A, 3B, 6C, 6D) or solid (4, 5A, 5B, 6A, 6B, 8) modular element, which can be a graft directly or substitute or a grafting substance.

Figure 1A:
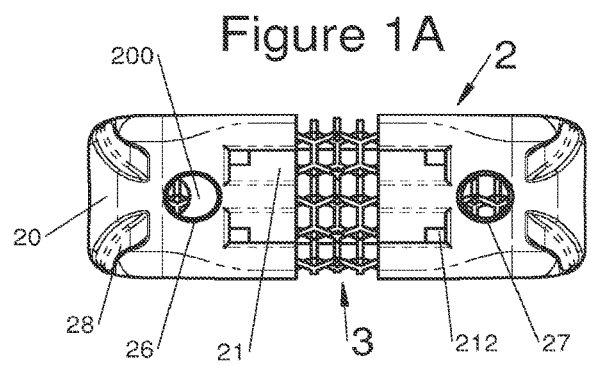
FIGS. 1A, 1B, 1C and 1D show respectively a view of the rear face, a profile view, a top view and a perspective view of an intervertebral implant including a graft insert according to one embodiment.
Figure 1B:
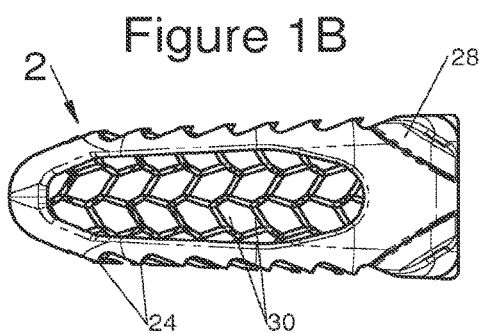
Figure 2A:
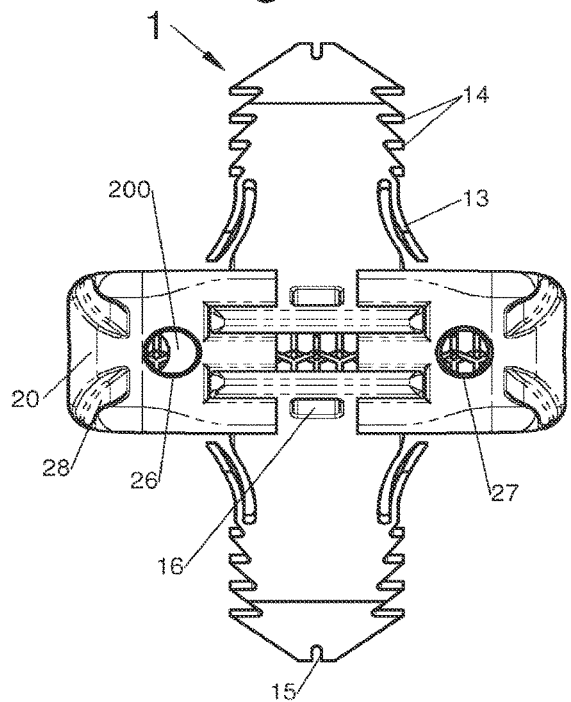
FIGS. 2A, 2B, 2C and 2D show respectively a view of the rear face, a top view and a perspective view of an intervertebral implant including a graft insert and provided with two anchoring devices according to one embodiment.
Figure 2B:
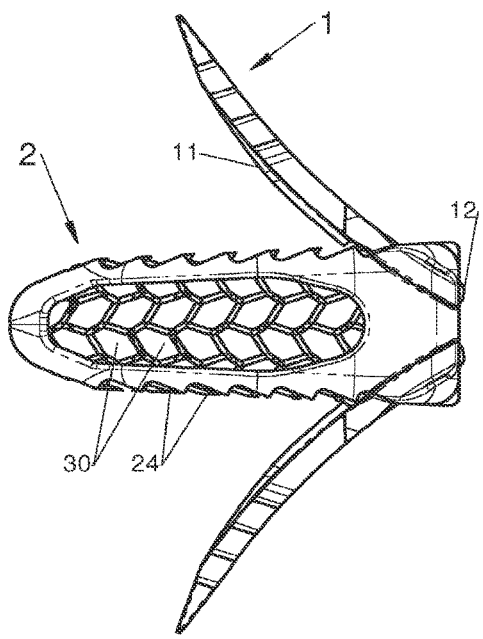
Figure 2C:
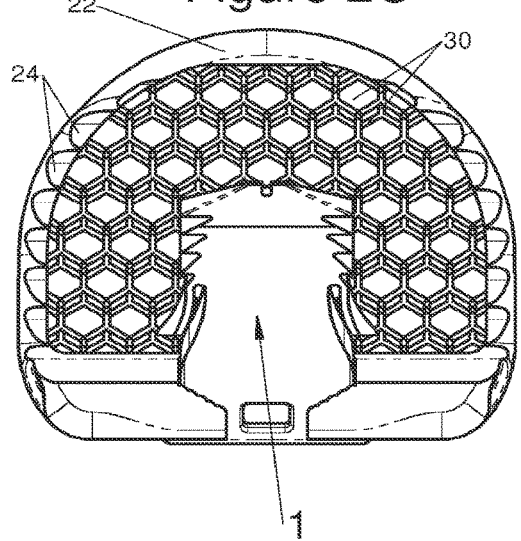
Figure 2D:
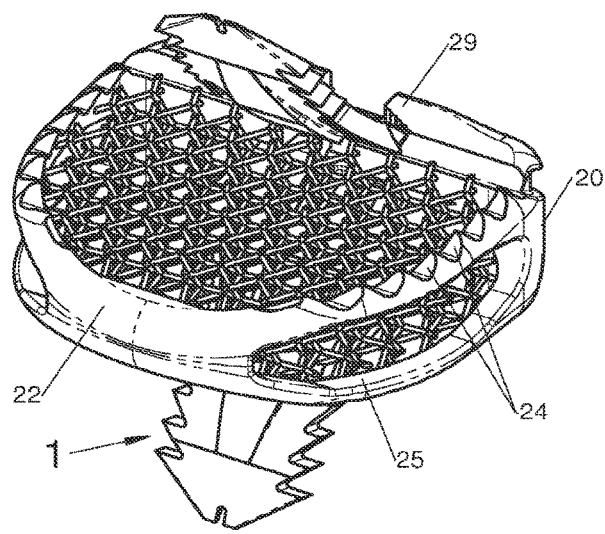

In certain embodiments, the meshed modular element (3, 3A, 3B, 6C, 6D) includes a three-dimensional network comprising interconnected adjacent planes, each plane being formed from meshes (30). The present application designates this type of structure by the term "meshed" or "with meshes" or "lattice," to illustrate the fact that these structure include at least one open network composed of points interconnected by ridges, which result in repeated patterns, more or less mutually identical, such as for example honeycomb or rectangular or lozenge networks or any type of network the meshes whereof can have various shapes, even within the same network or the same insert. In certain embodiments, as mentioned elsewhere in the present application, the network of meshes is configured so that the openings of a given plane of the network are aligned, in a predetermined direction, with those of other planes of the network, so that it is possible to see through the openings by looking in this predetermined direction and thus see through the implant. FIGS. 1B and 2B show advantageous examples of such alignments, which can be taken advantage of to monitor bone growth by viewing X-ray pictures taken in profile. As mentioned elsewhere in the present application, this type of network is generally easier to obtain with an additive manufacturing technique than with other techniques, such for example as machining or molding. Thus in certain embodiments, the three-dimensional network of the meshed modular element (3, 3A, 3B, 6C, 6D) is obtained by a three-dimensional printing or additive manufacturing technique. In certain embodiments, the meshed element (3, 3A, 3B, 6C, 6D) comprises at least a stabilization means (33, 32A, 32B), such as a cutout for example, allowing the element to adapt to, and/or assume, the shape of the body of the implant (2) and/or a reinforcement (202), as shown for example in FIGS. 7A, 8B and 9A, so as to stabilize the meshed modular element on (or in) the body of the implant. In certain embodiments, the meshed modular element comprises at least one locking means (31) arranged on at least one of the faces of said element, as shown for example in FIG. 9A. The locking element (31) can for example be formed from a clip, a staple, a hook or any similar element allowing locking and/or stabilizing the meshed modular element on the reinforcement (202) of the body of the implant (2). In certain embodiments, at least one graft insert (250) can be introduced (hence introduced during its use) preferentially into the implant, for example through at least one lateral opening, preferably so as to be locked into the implant, or so as to lock the latter. Preferably, the graft insert (250) is meshed (251B), for example so as to rapidly obtain bone fusion. Said insert (250) comprises at least one locking means (252A, 252B), which can in particular be formed by at least one clip, a hook or any similar element allowing locking and/or stabilizing the graft insert (250) on the lateral wall (25) of the implant. Moreover, the graft insert (250) generally comprises notches (251A) arranged over at least one of the upper and lower surfaces, particularly so as to improve the stability of the implant between the vertebrae and avoid any displacement of the implant between the vertebrae between which it is designed to be implanted, at least as long as bone fusion is not yet sufficient to immobilize the assembly.

In certain embodiments, the modular element (4, 5A, 6A, 6B, 8) has a tubular shape (for example FIGS. 5A, 5B, 8A, 8B) or any other shape adapted to its insertion into the body of the implant (for example FIGS. 5C, 5D, 7B, 18A, 18B), so as to reinforce the bone structure and/or accelerate bone fusion. It is therefore understood that a complementarity of shape is in fact provided between said element and said body of the implant. In certain embodiments, for example as shown in FIGS. 18A and 18B, a graft insert (8) comprises at least one supporting surface (83) bearing against at least one attachment insert (210) and/or at least one supporting surface (81) complementary with at least one surface, lower or higher for example, of the implant (2), and/or an extension (82) making it possible to fill, at least partially, at least one opening of the implant, for example in the lateral wall (25) and/or anterior or posterior wall of the implant. It will be noted that in these embodiments, the inserts (4, 5A, 6A, 6B, 8) can also be graft inserts, such for example as hollow, meshed or solid inserts, and they can fill the cavity of the implant partially or totally. In certain embodiments, the solid modular element can be inserted into a recess of a meshed modular element, as shown for example in a non-limiting manner in FIGS. 5A and 8B, and/or in a recess (60A) of a charging element, as shown for example in FIG. 5D. This type of arrangement makes it possible for example to reinforce the system and/or the bone structure and/or to accelerate bone fusion. Thus, different configurations allow the use of various types of interchangeable and not mutually exclusive graft (and/or attachment) inserts according to the needs of the patient and/or the desires of the surgeon.

In certain embodiments, the shapes and dimensions of said opening in at least one of said walls of the implant (2) are complementary, at least in one plane, to the shapes and dimensions of the graft insert (3, 3A, 3B, 4, 5A, 5B, 6A, 6B, 6C, 6D, 202, 250) and/or to the bone-anchoring insert (210). Thus, said opening allows the insertion of the graft insert (3, 3A, 3B, 4, 5A, 5B, 6A, 6B, 6C, 6D, 202, 250) and/or of the bone-anchoring insert (210) inside the body (20) of the implant (2). Thus, a meshed modular element (3, 3A, 3B, 6C, 6D) can be inserted easily by at least one translation, particularly vertical (for example as in FIGS. 10, 3D, 7A, 8B, 9A) and/or horizontal (for example as in FIGS. 4D, 5A, 6, 19A), for example through at least one opening in at least one of said walls of the implant (the lateral, posterior, upper and/or lower walls in the examples shown). Likewise a solid modular element (4, 5A, 5B, 6A, 6B, 8) can be inserted (preferably easily and quickly) by at least one translation, particularly vertical (for example as in FIGS. 7B and 8B) and/or horizontal (for example as in FIGS. 5B, 5D, 18A), through at least one opening of the implant (2). Moreover, as the implant (2) can include several openings on different faces, it is possible to provide that the different inserts be introduced by at least one of the various openings and be configured (mainly by their shapes and dimensions) not to be able to leave by at least one of the other openings, so that they are thus retained inside the implant. As an alternative or a complement, it is possible to provide shapes and dimensions of these elements so that the introduction of the inserts into the body is possible, while their departure is not, or at least that the former is easier than the latter. Thus, as described previously and hereafter, various embodiments are provided for providing the assembly and/or locking means (31, 252A, 252B, 203, 230B, 203C, 2030, 204A, 2040A, 204B, 2040B, 205, 255, 2155, 209A, 209B, 2090A, 2090B, 2070, 2080, 220, 2120), preferably complementary, between the implant and the inserts. For example, such means can be arranged on the graft inserts (3A, 3A, 3B, 4, 5A, 5B, 6A, 6B, 6C, 6D, 8, 202, 250) so as to facilitate the introduction and their attachment in the body of the implant and prevent the removal of said inserts from the body of the implant. The openings, in these various variants, are therefore complementary to the inserts, and conversely, in at least one plane, and preferably in a single plane, so that the inserts can be inserted into the implant without filling its entire cavity and/or while limiting the risks that they will unintentionally leave the implant.

In certain embodiments, said graft insert (3, 3A, 3B, 4, 5A, 5B, 6A, 6B, 6C, 6D, 8, 202, 250) forms a cover which does not fill said cavity of the implant, thus leaving free a portion of said cavity, for example for receiving bone graft or substitute. This cover can be formed by a meshed and therefore open graft insert of by a solid and therefore closed graft insert. This insert configuration makes it possible in particular to fill the implant with a larger quantity of graft, but also to choose to what degree the cavity should be filled, and especially to choose which are the faces of the implant which must remain open, closed by a cover or partially obstructed, particularly by the presence of an insert with a meshed structure, the density whereof can vary depending on needs. Thus, this type of configuration supplies a very extended range of possibilities for each of the openings of the implant, whether lateral, posterior, anterior, upper or lower. Moreover, various advantages can be obtained by the selection of the type of structure and material of the wall on the different faces of the implant and/or the selection of a contact between the graft and the bone structure. Thus, once again, the modularity of the different embodiments described in the present application supplies numerous advantages, particularly for the therapeutic selections of the surgeons. Moreover, various features combined together supply attractive synergies which only the modularity of the present implants make possible to exploit easily and freely. For example, an upper or lower wall made of titanium makes it possible to have a bone contact which is known to provide a high-performance bone attachment (and the more so if the titanium portion of the implant is rough, for example because it is obtained by additive manufacturing), and as a meshed wall which remains partially open allows preserving a satisfactory contact between the graft and the bone structure and/or satisfactory blood and/or cellular circulation, the probabilities of obtaining a reliable arthrodesis are increased by an insert with a meshed structure made of titanium, especially if this insert retains a good cavity in the implant to place substantial graft there. On the other hand, the fact of closing the lateral walls can make it possible to better contain the graft which must generally favor a mainly vertical arthrodesis, but as the visualization of bone growth is often desired, it can be preferred, for example for following-up with the patient, to select a lateral wall preserving good visibility of the interior of the implant, but sometimes also capable of containing the graft or even sometimes a structure partially open and closed. Moreover, FIG. 1B illustrates an example of meshing offering a particularly advantageous visibility in a lateral view of the implant. This visibility is obtained by the fact that the spaces between the successive meshes in a given direction are aligned with one another, so as to provide increased visibility, even unobstructed visibility from one side to the other. Moreover, the modularity of the implant also makes it possible to choose which are the faces through which the graft will be loaded into the implant and to choose the compression that it is desired to exert on the graft to improve its contact with the patient's bone. For example, it is sometimes advantageous to provide implants intended for loading the graft through the upper or lower surface, because this method seems to allow an improvement of the contact between the graft and the vertebrae while offering good compression of one on the other.

Figure 14A:
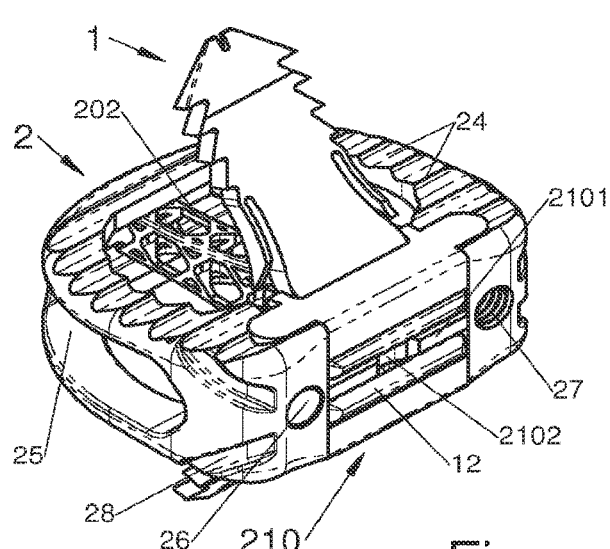
Figure 14B:
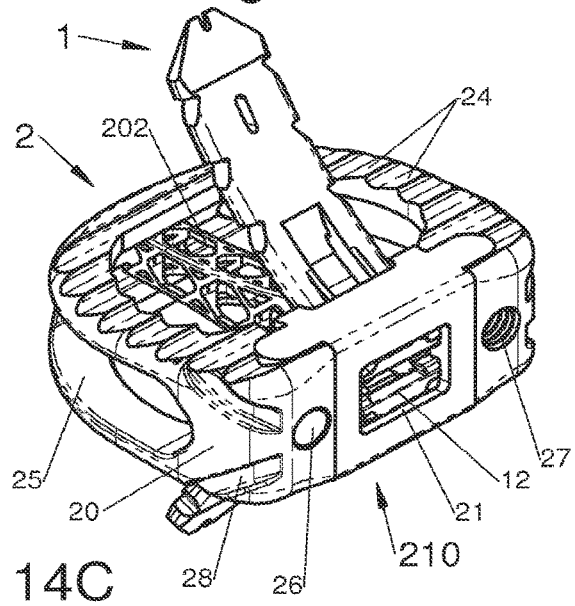
Figure 14C:
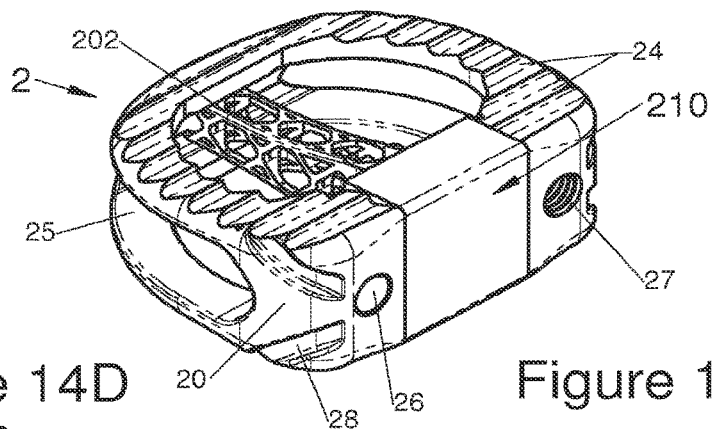
Figure 14D:
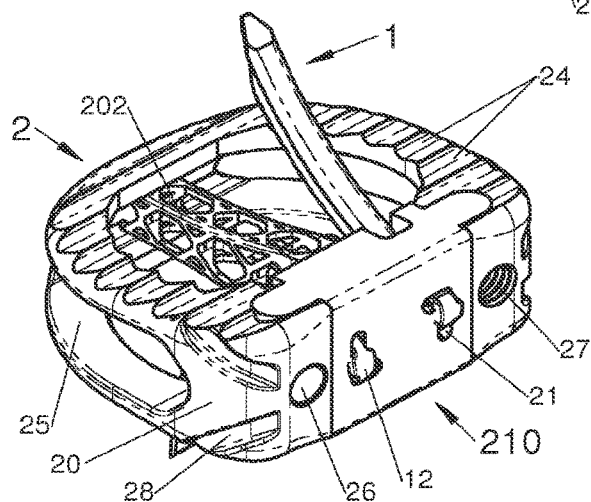
Figure 14E:
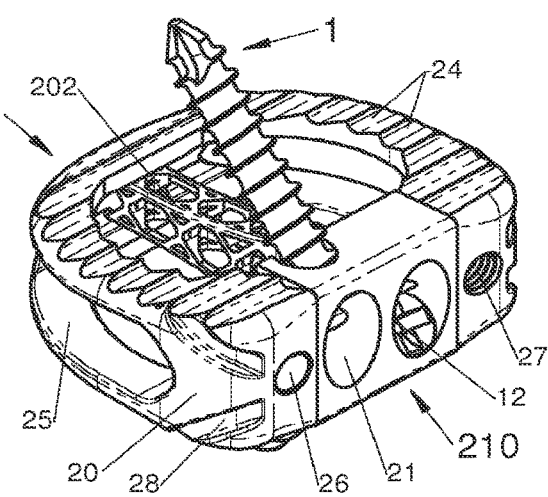

It is understood that the different embodiments further respond to the problem of stability by bone-anchoring, generally thanks to at least one passage (21) in the implant (in its body or in its anchoring insert). The passage (21), whether it is provided directly in the body (20) of the implant or in the attachment insert, is generally configured to accommodate at least one anchoring device (1), preferably rigid and curved (for example in the form of a plate) so as to allow the passage of this anchoring device (1), preferably without deformation despite its curvature. This passage (21) passes through the implant (2) from the periphery to an upper or lower surface, preferably along a rectilinear (or generally composed of at least two coplanar rectilinear portions forming an angle between them) and oblique trajectory suited to the curvature of the anchoring device (1) so as to orient the anchoring device (1) in the direction of the bone in which the anchoring device (1) must be attached. Moreover, as mentioned previously, the anchor is preferably elongated along a longitudinal axis which extends between a first end, designated here as the "anterior end," designed to penetrate into a bone (generally a vertebra) and a second end, designated here as the "posterior end," generally designed to remain in the implant to retain it, to hold it in place, which remains true generally for anchoring through a passage which is directly in one of the walls of the body of the implant itself or of an insert added to the body. In certain embodiments, the implant (2) includes at least one abutment (212, FIG. 1A) comprising at least one abutment surface, for example in the interior or just at the entrance of the passage (21) and oriented in the direction of the exterior of the implant (2) and designed to cooperate with at least one abutment (12) of the anchoring device (1) so that this abutment (12) stops the movement of the anchoring device (1) in the implant when it is sufficiently anchored in a vertebra through the passage (21), as shown for example in FIG. 2B or 14A, 14B, 14D or 14E and as known in the prior art, particularly prior applications of the applicant of the present application. This mechanism potentially allows the implant (2) to be retained against the bone, in particular the vertebra. On the other hand, in certain embodiments, the anchoring device (1) includes at least one retaining abutment (13, 112) (or withdrawal abutment) preventing it from moving backward (or limiting the risks of it moving backward) inside the passage (21) once anchored in the vertebra through the implant. This abutment can be formed for example by a tab or a flexible latch (13) of the anchoring device (4) or of the implant (2) which is pushed back when the anchoring device (1) is sliding in the passage (21) to place itself in abutment against a complementary surface (29), respectively of the implant (2) or of the anchoring device (1). Thus, in a complementary manner, the vertebral implant (2) can include, for example on the upper surface and/or on the lower surface of the body (20), at least one abutment surface (29, 29A) so as to retain the body (10) of the anchoring device (1). Likewise, the vertebral implant (2) can include at least one abutment surface (29b) so as to retain a graft insert (3, 3A, 3B, 4, 5A, 5B, 6A, 6B, 6C, 6D, 8, 202, 250) of the body of the implant (2), for example on the upper and/or lower surface of the body (20), for example at or in proximity to the anterior end. Preferably, this abutment surface is in proximity to the posterior portion of the body (20), at the exit or in proximity to the exit of the passage (21) in the direction of the upper surface and/or the lower surface. This abutment can be formed from lateral tabs, for example as shown in FIG. 14A, or by a central tongue, for example as in FIG. 14B, but other variants are possible. In particular, anchors locked by a latch housed in the implant are known and it is possible to provide the same mechanism in an insert of the type of those described here. On the other hand, this type of abutment can take the form of at least one abutment surface (211) outside the passage (21) and cooperating with a notch (112) of a rib (11) (or of a second plate) of the anchoring device (1). In certain embodiments, the body (20) includes two passages (21) each oriented toward one of the surfaces, upper and lower, of the implant (2), so as to allow the anchoring of an anchoring device (1) in each of the vertebrae between which the implant (2) is designed to be implanted. In certain embodiments, the attachment insert (210) comprises at least one abutment surface (2101) separating two passages (21) and on which the posterior portion (12) of the anchoring device (1) is supported, said abutment (2101) making it possible to hold stable the device (1) implanted in the vertebra through the passage (21), for example as shown in FIG. 10A, 11A, 12A or 14A. In certain embodiments, this vertebral attachment insert (210) comprises at least one access, for example a hollow (2102), separating two abutment surfaces (2101). In certain embodiments, the posterior end of the reinforcement (202) also comprises an access, for example a protrusion or a hollow or a recess (2071) designed to be opposite the hollow (2102) of the attachment insert (210) when the latter is attached to the implant (2). In certain embodiments, the posterior end of the reinforcement (202) also comprises an access, for example a protrusion, or a hollow or a recess (2071) designed to be opposite the hollow (2102) of the attachment insert (210) when the latter is attached to the implant (2). This type of hollow or recess provides in fact an access to the anchor, particularly to the abutments, allow them to be pulled on and withdraw it if needed. In certain embodiments, the attachment insert (210) comprises a passage (21) constituted of at least one abutment (2104A, 2104B) making it possible to hold the anchoring device (1) implanted in the vertebrae through the passage (21), for example as shown in FIGS. 20A to 20F.

It will be understood that anchors of different types can involve different embodiments of the implant designed to receive them, either directly or via an anchoring insert as shown for example by the diversity of the embodiments illustrated in FIGS. 14A, 14B, 14C, 14D and 14E which are not of course limiting and demonstrate exactly to what extent any type of bone anchoring is made possible by various embodiments presented here. In fact, these figures show five different embodiments various features whereof can be combined together. As explained previously, this diversity makes it possible to provide an infinite selection to surgeons at the lowest cost, for example for a low invasiveness or on the contrary a very deep anchorage or even a compressive anchorage, etc. Thus for example, FIG. 14A shows two anchorage devices in the form a plates provided with lateral withdrawal abutments, two anchoring devices in the form of plates provided with a central withdrawal abutment, no anchoring device, two L-section anchoring devices and two anchoring devices in the form of slotted point screws.

In certain embodiments, the body of the implant includes at least one opening capable of receiving at least one insert. In certain of these embodiments, the shapes and dimensions of said opening in at least one of said walls of the implant (2) are complementary to the shapes and dimensions of the graft insert (3, 3A, 3B, 4, 5A, 5B, 6A, 6B, 6C, 6D, 8, 202, 250) and/or to the bone-anchoring insert (210). Moreover, a coupling makes it possible to firmly attach the implant to this (or these) insert(s). Moreover, if the implant is intended to receive these two types of inserts, they are preferably for their part also designed to be mutually complementary, or so that a coupling allows them to be firmly attached together.

In certain embodiments, the posterior portion of the body (20) of the implant (2) comprises an opening (20P) capable of receiving said bone-anchoring insert (210). In certain embodiments, said opening (20P) extends from the upper surface to the lower surface of the body (20) and provides a space between two opposite surfaces (20S) in the walls of the posterior portion of the body (20). The figures of the plates 10, 11, 12, 13, 14, 15, 16, 17 and 18 show examples of such an arrangement, which has the advantage of supplying an anchorage insert of a substantial size with respect to the implant and capable of receiving a satisfactory anchoring. In certain embodiments, the reciprocal locking means (203, 2030, 204A, 2040A, 204B, 2040B, 220, 2120, 2050, 2070, 2080, 2090A, 2090B, 2155) of said bone-anchoring insert (210) in the implant (2) are arranged inside said opening (20P) and on the edges of said bone-anchoring insert (210). Various embodiments are shown on these different plates to illustrate the numerous possibilities. Among these various embodiments can be mentioned, in a non-limiting manner, a particular embodiment, in which the attachment insert (210) comprises at least one female locking means (2070) complementary to at least one male locking means (207) of the reinforcement (202) of the implant (2). Said female locking means, a recess (2070) for example, is delimited by at least one lip (2080) and capable of receiving the male locking means, such as a protrusion, for example toward the posterior end (207), as shown for example in a non-limiting manner in FIGS. 15A, 15B and 15C. Thus, the recess (2070) of the attachment insert (210) is capable of attaching itself in a stable manner to the posterior end (207) of the reinforcement (202) of the implant (2). It will be noted that it is possible to reverse the locking configuration of the attachment insert on the implant, i.e. to provide a male locking means on the attachment insert which will be complementary to a female locking means on the reinforcement of the implant, thus allowing variation of the attachment combinations of the attachment insert on the implant. In certain embodiment, the attachment insert (210) comprises at least one male locking means (for example a rib, a protrusion, a profile, a tongue, an abutment, a boss, a tenon or their combinations; these examples of course being valid for all the male elements described in the present application, identified in particular under reference symbols: 2040A, 2040B, 2050, 2090A, 2090B, 2130B, 2130C, 2155), complementary to at least one female locking means of the implant (2) (for example a groove or a recess or an opening or any equivalent, these examples of course also being valid in all of the present application, including for the elements identified under reference symbols: 205, 209A, 209B, 230B, 230C, 255), for example as shown in a non-limiting manner in FIGS. 11A to 11C, 12A to 12C, 13A, 13B, 16A, 16B, 16D, 18A, 18B and 20E. The male locking means is inserted, preferably easily, by translation, sliding and/or clipping, into the female locking means so as to attach the attachment insert to the implant in a stable manner (on the posterior end of the implant). In order to reinforce and maintain the stability of the attachment of the attachment insert to the implant, the attachment insert (210) can comprise a hollow (2130A) making it possible to separate the male locking means (2130B, 2130C) and possibly supply a support for at least one abutment surface (230A) of the implant (2), for example a posterior surface. It will be noted that it is also possible to stabilize the attachment of the attachment insert to the implant, for example by arranging said male locking means (2040A, 2040B, 2050, 2090A, 2090B, 2130B, 2130C, 2155) in the implant or the reinforcement of the implant, for example so that said female locking means (205, 209A, 209B, 230B, 230C, 255) is complementary to the attachment insert. This type of locking means avoids having the attachment insert dissociate itself from the implant and, preferably, also prevents the graft inserts (3, 3A, 3B, 4, 5A, 5B, 6A, 6B, 6C, 6C, 6D, 8, 202, 250) contained in the body of the implant (2) from becoming detached.

In certain embodiments, said bone-anchoring insert (210) and said body (20) of the implant (2) include reciprocal locking means (203, 2030, 204A, 2040A, 204B, 2040B, 220, 2120, 2050, 2070, 2080, 2090A, 2090B, 2155) of said bone-anchoring insert (210) in the implant (2). In fact, different embodiments provide for assembly of the implant with the insert. The present application can therefore also relate to a method of implantation or, more generally, a method for preparing implants prior to implantation. In fact, supply of the different elements capable of assembly, whether it is implemented by supplying separately or as a kit, must be considered as being within the scope of the application, and the method of assembly flows naturally from the functional considerations provided by the present application. Various embodiments allow assembly in situ, i.e. during the course of the implantation, particularly because the assembly of an insert with the implant is accomplished substantially within the plane of the antero-posterior axis as defined in the present application. The figures of plate 15 and of plate 18 are good, non-limiting examples thereof, but the figures of plates 16 or 19 and 20 show that various variants can be considered. In certain embodiments, the inserts and the implant are configured so that they are retained in the implant, for example by coupling means relying on insertion "by force" such as clipping. The fact of being able to assemble the components in this manner could allow assembly in situ, i.e. first inserting the skeleton into the patient, then loading the graft (insert or not), then inserting the anchor, then anchoring. Moreover, locking means can be provided so that the inserts do not detach themselves from the implant after assembly, for example as illustrated by FIGS. 13D, 13E and 20A to 20F. In fact, in certain embodiments, it is possible to provide for at least one locking means, such as a part or a screw (7) for example, attached to the attachment insert (2010) and the implant (2) by at least one locking means, a recess for example (206, 2067), so as to immobilize the vertebral implant and the implanted insert between the vertebrae. In other embodiments, the locking means, such as a screw for example (2152) is attached to the attachment insert (210) and/or the reinforcement (202) and/or the implant (2), through a recess for example (52A, 52B), so as to lock and/or immobilize the attachment insert and the inserted implant between adjacent vertebrae. Thus, assembly prior to implantation is provided for so that the risks of dislocation are limited and the implant is made reliable, for example as illustrated in the figures of plate 17. When the direction in which the implantation is carried out is parallel, or identical, to that preferred for assembly, this assembly can easily be carried out in situ. On the other hand, when it is parallel but in the opposite direction, for example as in the figures of plate 19, in situ assembly remains possible but is less easy, while locking is then facilitated. Thus, coupling of the insert with the implant can be carried out so that they provide locking once the implant is implanted, because coupling and assembly must be carried out in a sequence which is not reproducible once the implant is implanted, like for example the sequences of translation, or even of pivoting and translation implied by the embodiments of the figures of plates 10, 11, 12, 13 or the closures by pivoting articulated portions of the body around at least one articulation axis, particularly as illustrated in a non-limiting manner in the figures of plates 21 and 22.

In certain embodiments, the graft insert (3, 3A, 3B, 4, 5B, 6A, 6B, 6C, 6D, 8, 202, 250) includes at least one solid or meshed reinforcement (202, 250). Such a reinforcement could for example include at least one bar extending from one wall to another of the implant, for example one peripheral wall to another, so as to reinforce the structure of the implant. The figures show examples of such a reinforcement arranged in the horizontal plane of the implant, but various orientations are possible depending on the type of implant and depending on the type of reinforcement that it is desired to obtain. In certain embodiments, it is the implant itself which includes this reinforcement formed directly inside the body of the implant, but it is advantageous to provide for it to also be modular, as a portion of the graft insert or as an independent structure. Moreover, it will be noted that this element is designated by the term reinforcement with reference to its function as a support for reinforcing the structure, but that this reinforcement also allows reinforcing the graft and/or the graft insert because it provides retention on which each of the latter can rest, or attach themselves, and which therefore reinforces their structure and their stability in the implant. Thus, according to various embodiments, the reinforcement will be an attachment reinforcement of the inserts or a supporting reinforcement in the implant or both at the same time. In certain embodiments, the upper and lower surfaces of the reinforcement (202) are located, respectively, lower and higher than the respectively upper and lower surfaces of the implant (2). This shape allows the implant (2) for example to assume possible irregularities of shape of the vertebral end-plates. Moreover, in certain cases, this shape allows the reinforcement, which is therefore set back with respect to the upper and/or lower surfaces, not to be in contact with the vertebral end-plates to avoid having it sink into the sponge-like bone in the center of the vertebral end-plate and so that only the walls of the implant support the loads by their contact with the more solid cortical bone. In certain embodiments, the reinforcement (202) comprises meshes (2020) allowing rapid bone fusion to be obtained. Moreover, notches (2023) can be provided on at least one of the upper and lower surfaces of the reinforcement, particularly to allow reinforcing the stability of the implant between the vertebrae (hence to avoid its displacement), particularly before bone fusion. In certain embodiments, the reinforcement (202) comprises at least one abutment surface (208) on which the attachment insert (210) bears at least partially, for example at the anterior end of this attachment insert (210). Said abutment makes it possible in particular to hold the reinforcement in the cavity of the implant attached between the vertebrae. In certain embodiments, the reinforcement (202) comprise a portion (2021) chamfered and/or beveled over at least a peripheral portion, for example at one of its upper and/or lower surfaces at least, so as to facilitate the insertion of the implant (2) between the vertebrae, for example as illustrated in FIGS. 19A and 19B.

In certain embodiments, the graft insert and/or the anchoring insert is configured to be complementary to at least one of the other elements of the implant, meaning that it cooperates reciprocally either with another insert (whether they are of the same type or different, in terms of anchoring and attachment), or with the implant, or with the reinforcement of the implant. Moreover, in certain cases, this cooperation allows these elements to cooperate in potentially providing synergy in at least one function. Thus, in certain embodiments, the meshed modular element (3, 3A, 3B, 6C, 6D) comprises at least one recess (35A) configured to receive at least one solid modular element (4, 5A, 5B, 6A, 6B) inside the cavity (23). For example, FIGS. 5A and 5D or 8B show examples of mutually complementary inserts, particularly with an insert introduced inside another for support or other functions relative to the problems in question. In other configurations representative of this type of cooperation, the meshed modular element (3) can comprise at least one recess (35B) capable of receiving and/or assuming the shape of at least one reinforcement (202). For example, FIGS. 9A and 10C show cooperation between at least one insert and at least one reinforcement. Finally, as already mentioned to again illustrate other examples of coupling and/or of reciprocal locking between insert and implant, FIGS. 7A, 7B, 9A and 19B show cooperation between at least one insert and the implant which accommodates them. Various coupling and/or cooperation means thus stabilize the assembly provided by various embodiments.

Figure 1C:
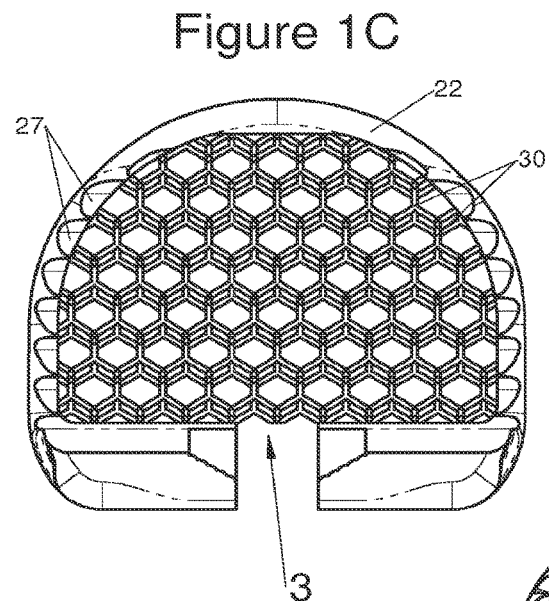
Figure 1D:
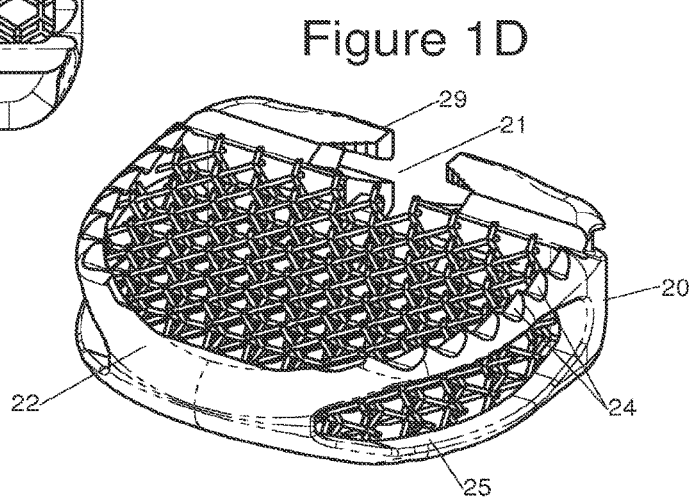

In certain embodiments, at least one of the upper and lower surfaces of the body (20) includes notches (24), for example as illustrated on most of the figures, to avoid displacement of the implant (2) between the vertebrae between which it is designed to be implanted, before bone growth is sufficient. Moreover, in various embodiments, the body (20) includes at least one portion (22) that is beveled and/or chamfered over at least a peripheral portion of at least one of its upper and lower surfaces, so as to facilitate the insertion of the implant (2) between the vertebrae, for example as illustrated in most of the figures, particularly FIGS. 1C, 3C, 6A etc. On the other hand, in certain embodiments, the posterior portion of the body (20) includes at least one attachment means designed to cooperate with a gripping end of an implantation instrument of the implant (2). The attachment means can comprise for example an oblique opening (200), as shown for example in FIGS. 1A and 2A, allowing gripping and/or holding (preferably fixed) of the implant during the surgical intervention. Preferably, two means (26, 27) are provided, one of the two attachment means preferably comprising an attachment and/or holding means in a direction not parallel to the axis of insertion of the implant, such for example as an oblique opening, which makes it possible in particular to facilitate handling in rotation. Moreover, at least one of these means can have a trajectory that is not parallel to the axis of implantation, so as to facilitate this type of handling and limit the risks of disengagement by movement parallel to the axis of implantation without requiring screwing the implant to the instrument which carries it using these attachment means. Moreover, stabilization means (28) can be provided, generally laterally, preferably on the edges of the implant. Finally, in certain embodiments, for example as shown in FIGS. 20C to 20F, the implant (2) comprises access means (241, 242B), such as openings or holes for example, so as to be able to inject graft or bone substitute, for example if this is considered necessary by the surgeon, particularly so as to improve the arthrodesis in the patient.

In certain embodiments, for example as shown in FIGS. 21A to 21D and 22A to 22E, the vertebral implant (2) comprises at least one actuating means (A2), such as a pivoting axis for example. Such a means particularly allows access to an opening of the implant for inserting the graft inserts (3, 3A, 3B, 4, 5A, 5B, 6A, 6B, 6C, 6D, 8, 202, 250), preferably easily and rapidly, into the cavity (23) of the implant (2) and/or allows the assembly of the inserts and the implant, so as to allow closure of the implant, subsequently forming a stable structure between the vertebrae. It will be noted that actuation, for example through the pivoting axis (A2), can be vertical, as shown for example in FIG. 21B, or horizontal, as shown for example in FIG. 22B. This actuation or pivoting axis allows the assembly, in a rapid and reliable manner, of the implant and the graft inserts designed to be implanted in the vertebra. These embodiments allow a pre-assembled kit to be offered, ready for surgical implantation, to save time for the surgeon during the surgical operation.

The present application describes various technical features and advantages with reference to the figures and/or to different embodiments. A person skilled in the art will understand that the technical features of a given embodiment can in fact be combined with features of another embodiment unless the contrary is explicitly stated or it is obvious that these features are incompatible or that the combination does not provide a solution to at least one of the technical problems mentioned in the present application. Moreover, the technical features describe in one given embodiment can be isolated from the other features of this embodiment unless the contrary is explicitly stated.

It must be obvious to persons skilled in the art that the present invention allows embodiments in numerous other specific forms without departing from the field of application of the invention as claimed. Consequently, the present embodiments must be considered by way of illustrations, but can be modified within the field defined by the scope of the appended claims, and the invention should not be limited to the details given above.

The invention claimed is:

1. An intervertebral implant comprising:
a body including a skeleton structure comprising open upper and lower surfaces and opposing side walls defining an interior cavity and including a respective opening through each of the opposing side walls into the interior cavity through each of the opposing side walls, the respective opening through each of the opposing side walls comprising a lattice structure, the interior cavity configured to receive one or more of a modular graft insert, bone graft, and substitute in a post-manufacturing process, wherein a leading end of the body comprises a solid beveled pointed edge and a trailing end of the body comprises a solid substantially flat edge, a height of the leading end being less than a height of the trailing end, the trailing end comprising first and second offset openings extending in a direction substantially parallel to an axis of insertion of the intervertebral implant and configured to receive a gripping end of an implantation instrument allowing gripping and/or holding of the intervertebral implant during surgical intervention;
first and second laterally elongated passages oriented transverse to the axis of insertion, each configured to receive a corresponding bone anchor including at least one of a screw and a curved plate body to anchor the intervertebral implant to an endplate of a vertebra; and
a reciprocal locking device that in an unlocked mode has a first angular orientation relative to a posterior wall and in a locked mode has a different second angular orientation relative to the posterior wall, wherein in the unlocked mode the reciprocal locking device is configured to enable each bone anchor to be moved forward and backward relative to a respective one of the first and second laterally elongated passages and in the locked mode the reciprocal locking device is configured to prevent each bone anchor from moving forward and backward once anchored in a vertebral surface.

2. The intervertebral implant of claim 1, wherein a passage through each of the open upper and lower surfaces is formed only in part by a second lattice structure and wherein the open upper surface comprises a first vertebral contacting wall of the body and the open lower surface comprises a second vertebral contacting wall of the body, the first and second vertebral contacting walls of the body being in an opposing relationship.

3. The intervertebral implant of claim 2, wherein the second laterally elongated passage extends from the posterior wall through to the second vertebral contacting wall of the body and in an opposing relationship to the first laterally elongated passage, the first laterally elongated passage extending from the posterior wall through to the first vertebral contacting wall of the body, and wherein the second laterally elongated passage is configured to receive a second bone anchor including at least one of a screw and a curved plate body to anchor the intervertebral implant to a second endplate of a second vertebra opposing the vertebra.

4. The intervertebral implant of claim 3, wherein the reciprocal locking device of the bone anchor and the body of the intervertebral implant locks a bone-anchoring insert in the intervertebral implant.

5. The intervertebral implant of claim 4, wherein the lattice structure and second lattice structure in the opposing side walls includes aligned openings in a plane to allow bone grow paths and enhanced medical imaging.

6. The intervertebral implant of claim 4, wherein a plurality of inserts are capable of being incorporated in said intervertebral implant through at least one opening in at least one of the said side walls, said plurality of inserts have at least two inserts selected from the following inserts: at least one graft insert having at least one solid or mesh reinforcement, the at least one graft insert being able to be colonised by bone tissue and/or to receive at least one bone tissue graft and/or at least one substitute.

7. The intervertebral implant of claim 6, wherein the reciprocal locking device rotates from the first angular orientation to the second angular orientation.

8. The intervertebral implant of claim 3, wherein the intervertebral implant comprises a laterally elongated passage extending from the trailing end of the body through to the open upper surface of the body, the open upper surface being a vertebral contacting wall of the body, wherein the laterally elongated passage is configured to receive a bone anchor including at least one of a screw and a curved plate body to anchor the intervertebral implant to an endplate of a vertebra, wherein the laterally elongated passage has an oblique trajectory relative to the axis of insertion.

9. The intervertebral implant of claim 8, wherein a plurality of openings into the interior cavity include the openings, a superior opening, and an opposing interior opening and wherein the lattice structure fills the superior opening and the opposing interior opening while leaving a portion of the interior cavity open between an opposing pair of lateral openings.

10. The intervertebral implant of claim 3, wherein the first laterally elongated passage and second laterally elongated passage each includes a recess to receive a flexible latch abutment on a bone anchor to lock the corresponding bone anchor into the first laterally elongated passage and/or second laterally elongated passage, respectively.

11. The intervertebral implant of claim 10, wherein the bone anchor and the body of the intervertebral implant has the reciprocal locking device to lock a bone-anchoring insert in the intervertebral implant.

12. The intervertebral implant of claim 1, wherein the lattice structure comprises a three-dimensional network of interconnected nodes and ridges defining planes of meshes.

13. The intervertebral implant of claim 1 wherein in the unlocked mode the reciprocal locking device has the first angular orientation relative to the solid substantially flat edge of the trailing end and in the locked mode has the different second angular orientation relative to the solid substantially flat edge of the trailing end.

14. The intervertebral implant of claim 1, wherein the plurality of openings into the interior cavity include the plurality of openings in each of the opposing side walls, a superior opening and an opposing interior opening.

15. The intervertebral implant of claim 1, wherein the lattice structure is selected from a plurality of interchangeable lattice structures.

16. The intervertebral implant of claim 1, wherein the skeleton structure defines an anterior wall including chamfered upper and lower surfaces to facilitate insertion of the intervertebral implant.

17. An implant system comprising:
an implant comprising a body including a skeleton structure defining an interior cavity and including a plurality of openings in each of the opposing side walls into the interior cavity through walls defined by the skeleton structure, the walls including a superior wall, an inferior wall, and opposing side walls and a substantially solid anterior wall and posterior wall, wherein openings of the plurality of openings in each of the opposing side walls are formed by lattice structures and the openings of the plurality of openings in the superior and inferior walls are formed only in part by lattice structures; and
a graft insert insertable into the skeleton structure in a post manufacturing process prior to implantation of the implant, wherein the anterior wall comprises a beveled pointed edge and the posterior wall comprises a substantially flat edge, a height of the beveled pointed edge being less than a height of the substantially flat edge, the posterior wall comprising first and second offset openings positioned along a midline of the posterior wall and extending in a direction substantially parallel to an axis of insertion of the implant and configured to receive a gripping end of an implantation instrument allowing gripping and/or holding of the implant during surgical intervention, wherein the superior wall comprises a first vertebral contacting wall of the body and the inferior wall comprises a second vertebral contacting wall of the body, the first and second vertebral contacting walls of the body being in an opposing relationship and further comprising a laterally elongated passage extending from the posterior wall through to the first vertebral contacting wall of the body, wherein the laterally elongated passage is configured to receive a bone anchor including at least one of a screw and a curved plate body to anchor the implant to an endplate of a vertebra.

18. The implant system of claim 17, wherein the lattice structures comprises a three-dimensional network of interconnected nodes and ridges defining planes of meshes.

19. The implant system of claim 18, wherein in an unlocked mode a reciprocal locking device has a first angular orientation relative to the posterior wall and in a locked mode has a different second angular orientation relative to the posterior wall and wherein in the unlocked mode the reciprocal locking device is configured to enable each bone anchor to be moved forward and backward relative to a respective one of first and second transverse laterally elongated passages and in the locked mode the reciprocal locking device is configured to prevent each bone anchor from moving forward and backward once anchored in a vertebral surface.

20. The implant system of claim 19, wherein the reciprocal locking device rotates from the first angular orientation to the second angular orientation.

* * * * *